US011918386B2

(12) United States Patent
Mulligan et al.

(10) Patent No.: US 11,918,386 B2
(45) Date of Patent: Mar. 5, 2024

(54) DEVICE-BASED MANEUVER AND ACTIVITY STATE-BASED PHYSIOLOGIC STATUS MONITORING

(71) Applicant: Flashback Technologies, Inc., Louisville, CO (US)

(72) Inventors: Isobel Jane Mulligan, Niwot, CO (US); Gregory Zlatko Grudic, Niwot, CO (US); Abhishek Jaiantilal, Highlands Ranch, CO (US)

( * ) Notice: Subject to any disclaimer, the term of this patent is extended or adjusted under 35 U.S.C. 154(b) by 446 days.

(21) Appl. No.: 16/726,334

(22) Filed: Dec. 24, 2019

(65) Prior Publication Data
US 2020/0205747 A1 Jul. 2, 2020

Related U.S. Application Data

(60) Provisional application No. 62/785,109, filed on Dec. 26, 2018.

(51) Int. Cl.
*A61B 5/00* (2006.01)
*A61B 5/01* (2006.01)
(Continued)

(52) U.S. Cl.
CPC ............. *A61B 5/7282* (2013.01); *A61B 5/01* (2013.01); *A61B 5/0205* (2013.01);
(Continued)

(58) Field of Classification Search
CPC ....... A61B 5/7282; A61B 5/01; A61B 5/0205; A61B 5/0531; A61B 5/1114;
(Continued)

(56) References Cited

U.S. PATENT DOCUMENTS 4,930,517 A    6/1990  Cohen et al.
5,074,310 A   12/1991  Mick
(Continued)

FOREIGN PATENT DOCUMENTS

CA      2871608       2/2021
WO   WO-2003-077854 A2   9/2003
(Continued)

OTHER PUBLICATIONS

Linder, S.P., Wendelken, S.M., Wei, E. et al. Using The Morphology of Photoplethysmogram Peaks to Detect Changes in Posture. J Clin Monit Comput 20, 151-158 (2006). https://doi.org/10.1007/s10877-006-9015-2 (Year: 2006).*

(Continued)

*Primary Examiner* — Carl H Layno
*Assistant Examiner* — Michael J Lau
(74) *Attorney, Agent, or Firm* — Capitol Patent + Trademark Law Firm, PLLC

(57) ABSTRACT

Novel tools and techniques are provided for physiological monitoring. A method includes receiving, with a computing system, physiological data of a user, analyzing, with the computing system, the received physiological data of the user to identify at least one of one or more body states or one or more transitions between body states of the user, and determining, with the computing system, at least one physiological state of the user, based at least in part on an analysis of the identified at least one of the one or more body states or the one or more transitions between body states of the user. The method further includes sending, with the computing system and to a user device, the determined at least one physiological state of the user, and displaying, on a display screen of the user device, the determined at least one physiological state of the user.

18 Claims, 7 Drawing Sheets

(51) Int. Cl.

| | | |
|---|---|---|
| *A61B 5/0205* | (2006.01) | |
| *A61B 5/0531* | (2021.01) | |
| *A61B 5/11* | (2006.01) | |
| *A61B 5/145* | (2006.01) | |
| *A61B 5/16* | (2006.01) | |
| *A63B 24/00* | (2006.01) | |
| *G10L 15/22* | (2006.01) | |
| *A61B 5/021* | (2006.01) | |
| *A61B 5/024* | (2006.01) | |
| *A61B 5/0295* | (2006.01) | |
| *A61B 5/08* | (2006.01) | |
| *A61B 5/318* | (2021.01) | |

(52) U.S. Cl.
CPC .......... *A61B 5/0531* (2013.01); *A61B 5/1114* (2013.01); *A61B 5/1116* (2013.01); *A61B 5/112* (2013.01); *A61B 5/14517* (2013.01); *A61B 5/165* (2013.01); *A61B 5/4803* (2013.01); *A61B 5/4875* (2013.01); *A61B 5/6803* (2013.01); *A61B 5/6807* (2013.01); *A61B 5/742* (2013.01); *A63B 24/0062* (2013.01); *G10L 15/22* (2013.01); *A61B 5/021* (2013.01); *A61B 5/02416* (2013.01); *A61B 5/0295* (2013.01); *A61B 5/0816* (2013.01); *A61B 5/318* (2021.01); *A61B 2560/0252* (2013.01); *A61B 2560/0257* (2013.01); *A61B 2562/0219* (2013.01); *A61B 2562/029* (2013.01); *G10L 2015/223* (2013.01)

(58) Field of Classification Search
CPC ... A61B 5/1116; A61B 5/112; A61B 5/14517; A61B 5/175; A61B 5/4803; A61B 5/4875; A61B 5/6803; A61B 2560/0252; A61B 2560/0257; A61B 2562/0219; A61B 2562/029; A63B 24/0062; G10L 15/22; G10L 2015/223
USPC ........................................................ 600/301
See application file for complete search history.

(56) References Cited

U.S. PATENT DOCUMENTS

| | | | |
|---|---|---|---|
| 5,213,099 | A | 5/1993 | Tripp, Jr. |
| 5,619,990 | A | 4/1997 | Kanai |
| 5,853,364 | A | 12/1998 | Baker, Jr. et al. |
| 5,865,168 | A | 2/1999 | Isaza |
| 5,967,981 | A | 10/1999 | Watrous |
| 5,984,893 | A | 11/1999 | Ward |
| 6,083,172 | A | 7/2000 | Baker, Jr. et al. |
| 6,094,592 | A | 7/2000 | Yorkey et al. |
| 6,206,830 | B1 | 3/2001 | Diab et al. |
| 6,248,080 | B1 | 6/2001 | Miesel |
| 6,338,713 | B1 | 1/2002 | Chamoun et al. |
| 6,371,921 | B1 | 4/2002 | Caro et al. |
| 6,398,728 | B1 | 6/2002 | Bardy |
| 6,409,675 | B1 | 6/2002 | Turcott |
| 6,411,833 | B1 | 6/2002 | Baker, Jr. et al. |
| 6,553,991 | B1 | 4/2003 | Isaza |
| 6,556,852 | B1 | 4/2003 | Schulze |
| 6,557,553 | B1 | 5/2003 | Borrello |
| 6,558,336 | B2 | 5/2003 | Collins |
| 6,589,189 | B2 | 7/2003 | Meyerson et al. |
| 6,591,122 | B2 | 7/2003 | Schmitt |
| 6,606,509 | B2 | 8/2003 | Schmitt |
| 6,675,031 | B1 | 1/2004 | Porges et al. |
| 6,721,584 | B2 | 4/2004 | Baker, Jr. et al. |
| 6,739,337 | B2 | 5/2004 | Isaza |
| 6,852,083 | B2 | 2/2005 | Caro et al. |
| 7,160,250 | B2 | 1/2007 | Lemaire |
| 7,231,245 | B2 | 6/2007 | Greenwald et al. |
| 7,285,100 | B2 | 10/2007 | Lemaire |
| 7,455,643 | B1 | 11/2008 | Li et al. |
| 7,547,283 | B2 | 6/2009 | Mourad et al. |
| 7,496,393 | B2 | 11/2009 | Diab et al. |
| 7,647,185 | B2 | 1/2010 | Tarassenko et al. |
| 7,654,964 | B1 | 2/2010 | Kroll et al. |
| 7,668,579 | B2 | 2/2010 | Lynn |
| 7,678,507 | B2 | 3/2010 | Berkow et al. |
| 7,720,516 | B2 | 5/2010 | Chin et al. |
| 7,865,224 | B2 | 1/2011 | Baker, Jr. et al. |
| 7,873,497 | B2 | 1/2011 | Weber et al. |
| 7,887,502 | B2 | 2/2011 | Ross et al. |
| 7,931,559 | B2 | 4/2011 | Baker, Jr. et al. |
| 7,957,780 | B2 | 6/2011 | Lamego et al. |
| 7,976,472 | B2 | 7/2011 | Kiani |
| 8,019,400 | B2 | 9/2011 | Diab et al. |
| 8,463,346 | B2 | 6/2013 | Kuhn et al. |
| 8,512,260 | B2 | 8/2013 | Grudic et al. |
| 8,641,635 | B2 | 2/2014 | Melker et al. |
| 9,603,534 | B2 | 3/2017 | Gabbay et al. |
| 9,757,041 | B2 | 9/2017 | Grudic et al. |
| 10,226,194 | B2 | 3/2019 | Grudic et al. |
| 2001/0027335 | A1 | 10/2001 | Meyerson et al. |
| 2003/0060690 | A1 | 3/2003 | Jelliffe et al. |
| 2003/0125612 | A1 | 7/2003 | Fox et al. |
| 2003/0130570 | A1 | 7/2003 | Krivitski et al. |
| 2003/0176931 | A1 | 9/2003 | Pednault et al. |
| 2003/0200189 | A1 | 10/2003 | Meng et al. |
| 2003/0212678 | A1 | 11/2003 | Bloom et al. |
| 2004/0215244 | A1 | 10/2004 | Marcovecchio et al. |
| 2004/0242972 | A1 | 12/2004 | Adak et al. |
| 2004/0267145 | A1 | 12/2004 | David et al. |
| 2005/0015009 | A1 | 1/2005 | Mourad et al. |
| 2005/0209516 | A1 | 9/2005 | Fraden |
| 2005/0228298 | A1 | 10/2005 | Banet et al. |
| 2006/0058691 | A1 | 3/2006 | Kiani |
| 2006/0064037 | A1 | 3/2006 | Shalon et al. |
| 2006/0106743 | A1 | 5/2006 | Horvitz |
| 2006/0161403 | A1 | 7/2006 | Jiang et al. |
| 2006/0166176 | A1 | 7/2006 | Lakin et al. |
| 2006/0178585 | A1 | 8/2006 | Sharrock |
| 2006/0253016 | A1 | 11/2006 | Baker, Jr. et al. |
| 2007/0015972 | A1 | 1/2007 | Wang et al. |
| 2007/0032732 | A1 | 2/2007 | Shelley et al. |
| 2007/0099239 | A1 | 5/2007 | Tabibiazar et al. |
| 2007/0112275 | A1 | 5/2007 | Cooke et al. |
| 2007/0213619 | A1 | 9/2007 | Linder |
| 2008/0039731 | A1 | 2/2008 | McCombie et al. |
| 2008/0045845 | A1 | 2/2008 | Pfeiffer et al. |
| 2008/0067132 | A1 | 3/2008 | Ross et al. |
| 2008/0077023 | A1 | 3/2008 | Campbell et al. |
| 2008/0097173 | A1 | 4/2008 | Soyemi et al. |
| 2008/0133434 | A1 | 6/2008 | Asar et al. |
| 2008/0146890 | A1 | 6/2008 | LeBoeuf et al. |
| 2008/0146892 | A1 | 6/2008 | LeBoeuf et al. |
| 2008/0154814 | A1 | 6/2008 | Chaudhury et al. |
| 2008/0234607 | A1 | 9/2008 | Hunter-Jones et al. |
| 2008/0294217 | A1 | 11/2008 | Lian et al. |
| 2009/0005703 | A1 | 1/2009 | Fasciano |
| 2009/0036754 | A1 | 2/2009 | Pons et al. |
| 2009/0069647 | A1 | 3/2009 | McNames et al. |
| 2009/0112106 | A1 | 3/2009 | Zhang |
| 2009/0143656 | A1 | 6/2009 | Manwaring et al. |
| 2009/0149724 | A1 | 6/2009 | Mark et al. |
| 2009/0149751 | A1 | 6/2009 | Mourad et al. |
| 2009/0204162 | A1 | 8/2009 | Addison et al. |
| 2009/0264776 | A1 | 10/2009 | Vardy |
| 2009/0272678 | A1 | 11/2009 | Sornmo et al. |
| 2009/0281434 | A1 | 11/2009 | Messerges |
| 2009/0287105 | A1 | 11/2009 | Hirsch |
| 2009/0292198 | A1 | 11/2009 | Kleiven et al. |
| 2009/0043222 | A1 | 12/2009 | Chetham |
| 2010/0016739 | A1 | 1/2010 | Shelley et al. |
| 2010/0041962 | A1 | 2/2010 | Causevic et al. |
| 2010/0081942 | A1 | 4/2010 | Huiku |
| 2010/0094158 | A1 | 4/2010 | Solem et al. |
| 2010/0160795 | A1 | 6/2010 | Banet et al. |
| 2010/0191128 | A1 | 7/2010 | Shelley et al. |
| 2010/0204589 | A1 | 8/2010 | Swoboda et al. |
| 2010/0249559 | A1 | 9/2010 | Lovejoy |

(56) References Cited

U.S. PATENT DOCUMENTS

| | | | |
|---|---|---|---|
| 2010/0298656 A1* | 11/2010 | McCombie | A61B 5/1118 600/595 |
| 2011/0077532 A1 | 3/2011 | Kim et al. | |
| 2011/0112799 A1 | 5/2011 | Weber et al. | |
| 2011/0152651 A1 | 6/2011 | Berkow | |
| 2011/0160549 A1 | 6/2011 | Saroka et al. | |
| 2011/0172545 A1 | 7/2011 | Grudic et al. | |
| 2011/0201962 A1 | 8/2011 | Grudic et al. | |
| 2011/0282169 A1 | 8/2011 | Grudic et al. | |
| 2011/0237914 A1 | 9/2011 | Lamego et al. | |
| 2012/0123232 A1 | 5/2012 | Najarian et al. | |
| 2012/0136224 A1 | 5/2012 | Najarian et al. | |
| 2012/0184840 A1 | 7/2012 | Najarian et al. | |
| 2012/0245439 A1 | 9/2012 | Andre' et al. | |
| 2012/0269420 A1 | 10/2012 | Najarian et al. | |
| 2012/0296219 A1 | 11/2012 | Chon et al. | |
| 2012/0330117 A1* | 12/2012 | Grudic | G16H 50/30 600/323 |
| 2013/0041268 A1 | 2/2013 | Rimoldi et al. | |
| 2013/0218056 A1 | 8/2013 | Aelen et al. | |
| 2013/0245397 A1 | 9/2013 | Grudic et al. | |
| 2013/0261468 A1 | 10/2013 | Semler et al. | |
| 2013/0343585 A1 | 12/2013 | Bennett et al. | |
| 2014/0073938 A1 | 3/2014 | Rodriguez-Llorente et al. | |
| 2014/0107437 A1 | 4/2014 | Pinsky | |
| 2014/0236053 A1 | 8/2014 | Walker et al. | |
| 2015/0065826 A1* | 3/2015 | Mulligan | A61B 5/7246 600/323 |
| 2015/0073723 A1* | 3/2015 | Mulligan | A61B 8/488 702/19 |
| 2015/0088431 A1* | 3/2015 | Podhajsky | A61B 5/443 600/479 |
| 2015/0141769 A1 | 5/2015 | Mulligan et al. | |
| 2016/0015284 A1 | 1/2016 | Grudic et al. | |
| 2016/0038042 A1 | 2/2016 | Mulligan et al. | |
| 2016/0038043 A1 | 2/2016 | Mulligan et al. | |
| 2016/0162786 A1 | 6/2016 | Grudic et al. | |
| 2016/0195041 A1 | 8/2016 | Lynn et al. | |
| 2016/0287166 A1* | 10/2016 | Tran | A61B 5/74 |
| 2016/0354039 A1 | 12/2016 | Soto et al. | |
| 2016/0374625 A1 | 12/2016 | Mulligan et al. | |
| 2017/0007139 A9 | 1/2017 | Grudic et al. | |
| 2017/0042433 A1* | 2/2017 | Noh | A61B 5/14542 |
| 2017/0105682 A1* | 4/2017 | MacDonald | A61B 5/681 |
| 2017/0215016 A1 | 7/2017 | Dohmen et al. | |
| 2017/0258329 A1 | 9/2017 | Marsh | |
| 2017/0281020 A1* | 10/2017 | Mulligan | G16H 50/20 |
| 2017/0303799 A1 | 10/2017 | Grudic et al. | |
| 2017/0347177 A1 | 11/2017 | Masaki | |
| 2018/0042540 A1* | 2/2018 | Kinnunen | A61B 5/02433 |
| 2018/0192965 A1* | 7/2018 | Rose | G16H 80/00 |
| 2018/0214028 A1 | 8/2018 | Zhang et al. | |
| 2018/0263539 A1* | 9/2018 | Javey | A61B 5/1477 |
| 2018/0303351 A1* | 10/2018 | Mestha | A61B 5/0077 |
| 2018/0325466 A1* | 11/2018 | An | A61B 7/04 |
| 2019/0192077 A1 | 6/2019 | Kaiser et al. | |
| 2020/0205734 A1 | 7/2020 | Mulligan et al. | |

FOREIGN PATENT DOCUMENTS

| | | |
|---|---|---|
| WO | WO-2003-091421 A3 | 11/2003 |
| WO | WO-2005-055825 A1 | 6/2005 |
| WO | WO-2005-112756 A1 | 12/2005 |
| WO | WO-2007-011565 A1 | 1/2007 |
| WO | WO-2007-098957 A1 | 9/2007 |
| WO | WO-2007-117570 A2 | 10/2007 |
| WO | WO-2007-149533 A2 | 12/2007 |
| WO | WO-2010-009735 A2 | 1/2010 |
| WO | WO-2010-053743 A1 | 5/2010 |
| WO | WO-2010-117572 A2 | 10/2010 |
| WO | WO-2011-002904 A2 | 1/2011 |
| WO | WO-2011-050066 A2 | 4/2011 |
| WO | WO-2011-103102 A1 | 8/2011 |
| WO | WO-2011-109734 A1 | 9/2011 |
| WO | WO-2012-054880 A2 | 4/2012 |
| WO | WO-2012-166568 A3 | 12/2012 |
| WO | WO-2013-016212 A1 | 1/2013 |
| WO | WO-2014-149981 A1 | 9/2014 |
| WO | WO-2015-042484 A1 | 3/2015 |
| WO | WO-2015-069940 A1 | 5/2015 |
| WO | WO-2015-073909 A1 | 5/2015 |
| WO | WO-2015-073910 A1 | 5/2015 |
| WO | WO-2016-061542 A1 | 4/2016 |
| WO | WO-2016-061545 A1 | 4/2016 |
| WO | WO-2017-044868 A1 | 3/2017 |
| WO | WO-2017-218431 A1 | 12/2017 |

OTHER PUBLICATIONS

U.S. Appl. No. 16/726,337, Non-Final Office Action dated May 17, 2021; 79 pages.

U.S. Appl. No. 15/261,661, Final Office Action dated May 19, 2021, 25 pages.

U.S. Appl. No. 14/535,171, Final Office Action dated May 19, 2021, 22 pages.

U.S. Appl. No. 14/542,423, Final Office Action dated May 19, 2021, 21 pages.

U.S. Appl. No. 15/649,411, Non-Final Office Action, dated May 19, 2021, 21 pages.

U.S. Appl. No. 14/542,426, Final Office Action dated Jun. 1, 2021, 20 pages.

U.S. Appl. No. 15/620,701, Non-Final Office Action dated Jun. 6, 2021, 22 pages.

U.S. Appl. No. 14/885,891, Non-Final Office Action, dated Jun. 8, 2021, 23 pages.

U.S. Appl. No. 13/041,006, Non-Final Office Action dated Jul. 16, 2021; 32 pages.

U.S. Appl. No. 15/261,661, Non-Final Rejection dated Sep. 3, 2020, 22 pages.

U.S. Appl. No. 14/535,171, Non-Final Office Action dated Oct. 5, 2020, 21 pages.

U.S. Appl. No. 14/542,423, Non-Final Office Action dated Oct. 6, 2020, 21 pages.

U.S. Appl. No. 15/620,701, Non-Final Office Action dated Oct. 21, 2020, 20 pages.

U.S. Appl. No. 13/041,006, Final Rejection, dated Jan. 7, 2021; 30 pages.

U.S. Appl. No. 14/885,888, Final Office Action dated Mar. 30, 2021, 25 pages.

U.S. Appl. No. 16/726,337, Final Office Action dated Sep. 7, 2021, 68 pages.

U.S. Appl. No. 15/620,701, Final Office Action dated Oct. 26, 2021, 22 pages.

U.S. Appl. No. 14/542,423, Final Office Action dated May 18, 2020, 21 pages.

U.S. Appl. No. 13/041,006, Non-Final Rejection, dated Jun. 12, 2020; 29 pages.

U.S. Appl. No. 15/620,701, Final Office Action dated Jun. 22, 2020, 25 pages.

EPO Communication pursuant to Rules 71(3) dated Jun. 23, 2020, 57 pages.

U.S. Appl. No. 15/649,411, Non-Final Office Action, dated Jul. 29, 11 pages.

U.S. Appl. No. 14/885,891, Non-Final Office Action dated Aug. 6, 2020, 19 pages.

U.S. Appl. No. 14/885,888, Non-Final Office Action dated Aug. 6, 2020, 2019, 21 pages.

U.S. Appl. No. 14/542,426, Non-Final Office Action dated Aug. 6, 2020, 2019, 19 pages.

U.S. Appl. No. 16/726,337, Non-Final Office Action, dated Jan. 12, 2022, 62 pages.

International Search Report and Written Opinion prepared by the U.S. Patent and Trademark Office as International Searching Authority for PCT International Patent Application No. PCT/US09/62119, dated Feb. 3, 2010, 5 pages.

(56) References Cited

OTHER PUBLICATIONS

International Preliminary Report on Patentability prepared by the International Bureau for PCT/US2009/062119, dated May 12, 2011, 6 pages.
Decision to Grant, dated Apr. 23, 2015 for EP 09825222.4, 3 pages.
European Search Report, dated Jun. 15, 2012 for EP 09825222.4, 10 pages.
Procopio et al (2008) Intelligent Robots and Systems IEEE/RSJ International Conference, pp. 620-627, "Learning in 1-14 dynamic environments with Ensemble Selection for autonomous outdoor robot navigation".
Shoemaker, et al (2001) CHEST, 120(2):528-538, "Outcome Prediction of Emergency Patients by Noninvasive Hemodynamic Monitoring".
Supplemental European Search Report, dated Jul. 3, 2012 for EP 09825222.4, 1 page.
U.S. Appl. No. 13/126,727, Non-Final Office Action dated Sep. 11, 2014; 58 pages.
U.S. Appl. No. 13/028,140, Non-Final Office Action dated Nov. 13, 2012; 27 pages.
U.S. Appl. No. 13/028,140, Notice of Allowance dated Feb. 22, 2013; 22 pages.
U.S. Appl. No. 13/028,140, Restriction Requirement dated Aug. 1, 2012; 7 pages.
U.S. Appl. No. 13/889,513, Non-Final Office Action dated Jun. 15, 2015, 27 pages.
International Preliminary Report on Patentability prepared by the International Bureau for PCT/US11/24938, dated Aug. 30, 2012, 7 pages.
International Search Report and Written Opinion prepared by the U.S. Patent and Trademark Office as International Searching Authority for PCT International Patent Application No. PCT/US2011/24938, dated Jun. 7, 2011, 13 pages.
Supplemental European Search Report, dated Jun. 21, 2013 for EP 11745124.5, 7 pages.
U.S. Appl. No. 13/041,006, Non-Final Office Action dated May 23, 2014; 27 pages.
U.S. Appl. No. 13/041,006, Non-Final Office Action dated Dec. 22, 2014; 14 pages.
International Preliminary Report on Patentability prepared by the International Bureau for PCT/US11/27237, dated Sep. 13, 2012, 10 pages.
International Search Report and Written Opinion prepared by the U.S. Patent and Trademark Office as International Searching Authority for PCT International Patent Application No. PCT/US2011/027237, dated May 27, 2011, 16 pages.
Cooke et al. (2004) Journal of Applied Physiology 96(4):1249-1261, "Lower body negative pressure as a model to study progression to acute hemorrhagic shock in humans".
Extended European Search Report, dated Oct. 18, 2013 for EP11751440.6, 7 pages.
Lambert et al. (2007) ACTA Anaesthesiologica Scandinavica 51(4):415-425, "Does a positive 1-27 end-expiratory pressure-induced reduction in stroke volume indicate preload responsiveness? An experimental study".
Ryan et al. (2008) Journal of Applied Physiology 104(5):1402-1409, "Breathing through an inspiratory threshold device improves stroke volume during central hypovolemia in humans".
Supplemental Extended European Search Report, dated Nov. 6, 2013 for EP11751440.6, 8 pages.
International Preliminary Report on Patentability prepared by the International Bureau for PCT International Patent Application No. PCT/US12/047659, dated Feb. 6, 2014, 10 pages.
International Search Report and Written Opinion prepared by the U.S. Patent and Trademark Office as International Searching Authority for PCT International Patent Application No. PCT/US12/47659, dated Oct. 12, 2012, 16 pages.
Extended European Search Report for EP 12816832.5, dated Oct. 6, 2014, 9 pages.
International Search Report and Written Opinion prepared by the Korean Intellectual Property Office as International Searching Authority for PCT International Patent Application No. PCT/US2014/064413, dated Feb. 12, 2015, 13 pages.
International Search Report and Written Opinion prepared by the Korean Intellectual Property Office as International Searching Authority for PCT International Patent Application No. PCT/US2014/065818, dated Feb. 26, 2015, 14 pages.
International Search Report and Written Opinion prepared by the Korean Intellectual Property Office as International Searching Authority for PCT International Patent Application No. PCT/US2014/065820, dated Feb. 26, 2015, 14 pages.
Berkow (Aug. 2010) Intelomed, Inc., "CVInsight," 14 pages.
Berkow (Jan. 2012) 510(K) Summary, "CVInsight," 9 pages.
Najarian (2012) VCU School of Engineering Research Report, vol. 5, p. 3.
U.S. Appl. No. 13/126,727, Final Rejection dated Aug. 27, 2015; 33 pages.
U.S. Appl. No. 13/041,006, Final Rejection dated Sep. 15, 2015; 19 pages.
Canadian Patent Application No. 2,775,675, Non-Final OA dated Dec. 9, 2015; 3 pages.
International Search Report and Written Opinion prepared by the Korean Intellectual Property Office as International Searching Authority for PCT International Patent Application No. PCT/US2015/056078, dated Jan. 25, 2016, 11 pages.
International Search Report and Written Opinion prepared by the Korean Intellectual Property Office as International Searching Authority for PCT International Patent Application No. PCT/US2015/56074, dated Jan. 29, 2016, 13 pages.
Convertino, Victor, "Estimation of individual-specific progression to impending cardiovascular instability using arterial waveforms," Journal of Applied Physiology, Oct. 15, 2013, vol. 115, No. 8, pp. 1196-1202.
U.S. Appl. No. 14/542,426 Non-Final Office Action dated Feb. 26, 2016; 25 pages.
U.S. Appl. No. 13/554,483, Non-Final Office Action dated Mar. 22, 2016; 41 pages.
EP11751440.6, Office Action 94(3) dated Feb. 24, 2016, 5 pages.
U.S. Appl. No. 13/041,006, Non-final Office Action dated Apr. 22, 2016, 15 pages.
International Preliminary Report on Patentability prepared by the International Bureau for PCT International Patent Application No. PCT/US14/064413, dated May 19, 2016, 10 pages.
International Preliminary Report on Patentability prepared by the International Bureau for PCT International Patent Application No. PCT/US14/65818, dated May 26, 2016, 11 pages.
International Preliminary Report on Patentability prepared by the International Bureau for PCT International Patent Application No. PCT/US14/65820, dated May 26, 2016, 11 pages.
Stewart et al. (2016) PubMed Epub ahead of print, "The Compensatory Reserve Index Following Injury: Results of a Prospective Clinical Trial" 2 pages.
U.S. Appl. No. 14/542,426, Final Office Action dated Sep. 26, 2016, 25 pages.
Intravenous Therapy (Wikipedia) Accessed on Sep. 27, 2016, 12 pages.
U.S. Appl. No. 13/554,483, Final Office Action dated Oct. 7, 2016, 28 pages.
International Search Report and Written Opinion prepared by the Korean Intellectual Property Office as International Searching Authority for PCT International Patent Application No. PCT/US2016/051130, dated Dec. 8, 2016, 14 pages.
U.S. Appl. No. 14/535,171, Non-Final OA dated Dec. 16, 2016, 37 pages.
U.S. Appl. No. 14/885,888, Non-Final OA dated Dec. 16, 2016, 35 pages.
Nadler et al. 2014, Shock 42(2): 93-98, "The Value of Noninvasive Measurement of the Compensatory Reserve Index in Monitoring and Triage of Patients Experiencing Minimal Blood Loss".

(56) References Cited

OTHER PUBLICATIONS

Nadler et al. 2017, Annals of Medicine and Surgery, "The approximated cardiovascular reserve index complies with haemorrhage related hemodynamic deterioration pattern: A swine exsanguination model" 7 pages.
Canadian Patent Application No. 2,775,675, Non-Final OA dated Nov. 9, 2016; 4 pages.
U.S. Appl. No. 13/041,006, Final OA dated Mar. 7, 2017, 21 pages.
U.S. Appl. No. 13/554,483, Notice of Allowance dated Mar. 7, 2017, 39 pages.
U.S. Appl. No. 13/889,513, Final Rejection dated Apr. 11, 2017; 51 pages.
Schmidt et al. (1997) Stroke, "Noninvasive Prediction of Intracranial Pressure Curves Using Transcranial Doppler Ultrasonography and Blood Pressure Curves," 22 pages.
International Preliminary Report on Patentability prepared by the International Bureau for PCT/US15/56074, dated Apr. 27, 2017, 10 pages.
International Preliminary Report on Patentability prepared by the International Bureau for PCT/US15/56078, dated Apr. 27, 2017, 7 pages.
U.S. Appl. No. 14/542,426, Non-Final Office Action dated May 5, 2017; 17 pages.
U.S. Appl. No. 14/542,423, Non-Final Office Action dated May 8, 2017; 35 pages.
U.S. Appl. No. 14/885,891, Non-Final OA dated May 18, 2017; 29 pages.
Extended European Search Report for EP14862697.1, dated Jun. 14, 2017; 8 pages.
U.S. Appl. No. 14/885,888, Final Office Action dated Jul. 27, 2017, 29 pages.
EP 11745124.5, Office Action 94(3) dated Jul. 31, 2017, 6 pages.
Kotsiantis (2007) Department of Computer Science and Technology, "Supervised Machine Learning: A Review of Classification Techniques," 20 pages.
Wu et al, (2009) World Congress on Computer Science and Information Engineering, "Time Series Mining Approach for Noninvasive Intracranial Pressure Assessment: an Investigation of Different Regularization Techniques," 5 pages.
Extended European Search Report, dated Jun. 7, 2017 for EP14862921.5, 8 pages.
Extended European Search Report, dated Jun. 20, 2017 for EP14859538.2, 8 pages.
International Search Report and Written Opinion prepared by the Korean Intellectual Property Office as International Searching Authority for PCT International Patent Application No. PCT/US2017/037067, dated Aug. 18, 2017, 21 pages.
U.S. Appl. No. 14/535,171, Final Office Action dated Nov. 16, 2017, 30 pages.
U.S. Appl. No. 13/889,513, Non-Final Office Action dated Dec. 1, 2017, 51 pages.
U.S. Appl. No. 14/867,938, Non-Final Office Action dated Dec. 8, 2017, 27 pages.
U.S. Appl. No. 13/041,006, Non-Final Office Action dated Dec. 15, 2017, 21 pages.
Canadian Patent Application No. 2,775,675, Non-Final OA dated Sep. 27, 2017; 4 pages.
U.S. Appl. No. 14/542,426, Non-Final Office Action dated Feb. 1, 2018, 19 pages.
U.S. Appl. No. 14/542,423, Non-Final Office Action dated Feb. 5, 2018, 24 pages.
U.S. Appl. No. 14/885,891, Non-Final OA dated Feb. 5, 2018, 22 pages.
Canadian Patent Application No. 2,871,608, Non-Final OA dated Jan. 25, 2018; 5 pages.
U.S. Appl. No. 14/885,888, Non-Final Office Action dated Mar. 15, 2018, 11 pages.
International Preliminary Report on Patentability prepared by the International Bureau for PCT/US2009/062119, dated Mar. 22, 2018, 9 pages.
U.S. Appl. No. 15/649,411, Non-Final OA dated Apr. 5, 2018, 23 pages.
Extended European Search Report for EP15850241.9, dated Apr. 5, 2018; 8 pages.
U.S. Appl. No. 15/007,489, Non-Final Office Action dated Jun. 13, 2018; 48 pages.
U.S. Appl. No. 14/535,171, Non-Final OA dated Aug. 9, 2018, 23 pages.
U.S. Appl. No. 14/867,938, Notice of Allowance dated Sep. 6, 2018; 17 pages.
U.S. Appl. No. 13/889,513, Final Office Action dated Sep. 20, 2018, 25 pages.
U.S. Appl. No. 14/542,426, Final Office Action dated Sep. 27, 2018, 11 pages.
U.S. Appl. No. 14/885,888, Final Office Action dated Sep. 28, 2018, 7 pages.
U.S. Appl. No. 14/885,891, Final Office Action dated Sep. 28, 2018, 10 pages.
U.S. Appl. No. 13/041,006, Final Office Action dated Oct. 3, 2018, 9 pages.
U.S. Appl. No. 15/261,661, Non-Final Office Action dated Oct. 12, 2018, 38 pages.
Canadian Patent Application No. 2,871,608, Non-Final OA dated Nov. 22, 2018, 3 pages.
European Patent Application No. 12816832.5, Non-Final OA dated Oct. 12, 2018, 4 pages.
International Preliminary Report on Patentability prepared by the International Bureau for PCT International Patent Application No. PCT/US2017/037067, dated Dec. 27, 2018, 13 pages.
U.S. Appl. No. 14/542,423, Non-Final Office Action dated Dec. 28, 2018, 18 pages.
EPO Communication pursuant to Rules 161(2) and 162 EPC dated Feb. 1, 2019, 4 pages.
Extended European Search Report for EP16845202.7, dated Feb. 1, 2019, 6 pages.
Moulton et al. (2013) Trauma Acute Care Surg 75(6): 1053-1059, "Running on empty? The Compensatory Reserve Index".
Poh et al. (2014) Experimental Physiology, 1421-1426, "Respiratory Pump Contributes to Increased Physiological Reserve for Compensation During Simulated Haemorrhage".
Extended European Search Report Written Opinion for EP16845202.7, dated Mar. 11, 2019, 8 pages.
EPO Communication pursuant to Rule 70(2) and 70(a)(2) EPC, dated Mar. 13, 2019, 1 page.
U.S. Appl. No. 15/007,489, Final Office Action dated Mar. 20, 2019, 36 pages.
U.S. Appl. No. 15/649,411, Non-Final OA dated Apr. 2, 2019, 24 pages.
U.S. Appl. No. 13/041,006, Non-Final OA dated Apr. 4, 2019, 15 pages.
U.S. Appl. No. 14/542,426, Non-Final OA dated Apr. 5, 2019, 9 pages.
U.S. Appl. No. 15/261,661, Final OA dated Apr. 5, 2019, 19 pages.
U.S. Appl. No. 13/889,513, Restriction Requirement dated Apr. 12, 2019, 9 pages.
U.S. Appl. No. 14/885,888, Non-Final Office Action dated May 15, 2019, 21 pages.
U.S. Appl. No. 14/885,891, Non-Final Office Action dated May 15, 2019, 18 pages.
U.S. Appl. No. 14/535,171, Final OA dated Jul. 3, 2019, 20 pages.
U.S. Appl. No. 14/542,423, Non-Final Office Action dated Jul. 9, 2019, 17 pages.
U.S. Appl. No. 15/620,701, Non-Final Office Action dated Aug. 12, 2019, 27 pages.
Japan Patent Application No. 2017-539521 Office Action, dated Sep. 5, 2019, 7 pages.
EP Application No. 15850241.9, EP Examination Report, dated Oct. 14, 2019, 6 pages.
U.S. Appl. No. 16/726,337 filed Dec. 24, 2019 by Mulligan et al. and entitled "Ear-Based Physiological State Monitoring" 78 pages.
U.S. Appl. No. 15/649,411, Final-OA dated Dec. 23, 2019, 19 pages.

(56) References Cited

OTHER PUBLICATIONS

U.S. Appl. No. 14/885,888, Final Office Action dated Jan. 2, 2020, 2019, 21 pages.
U.S. Appl. No. 14/542,426, Final-OA dated Dec. 20, 2019, 19 pages.
U.S. Appl. No. 15/261,661, Non-Final Rejection dated Jan. 16, 2020, 20 pages.
U.S. Appl. No. 14/535,171, Non-Final Rejection dated Jan. 23, 2020, 20 pages.
U.S. Appl. No. 13/041,006, Final Rejection dated Jan. 27, 2020; 10 pages.
U.S. Appl. No. 13/889,513, Non-Final-OA, dated Jan. 28, 2020, 27 pages.
U.S. Appl. No. 14/885,891, Final Office Action dated Mar. 3, 2020, 19 pages.

\* cited by examiner

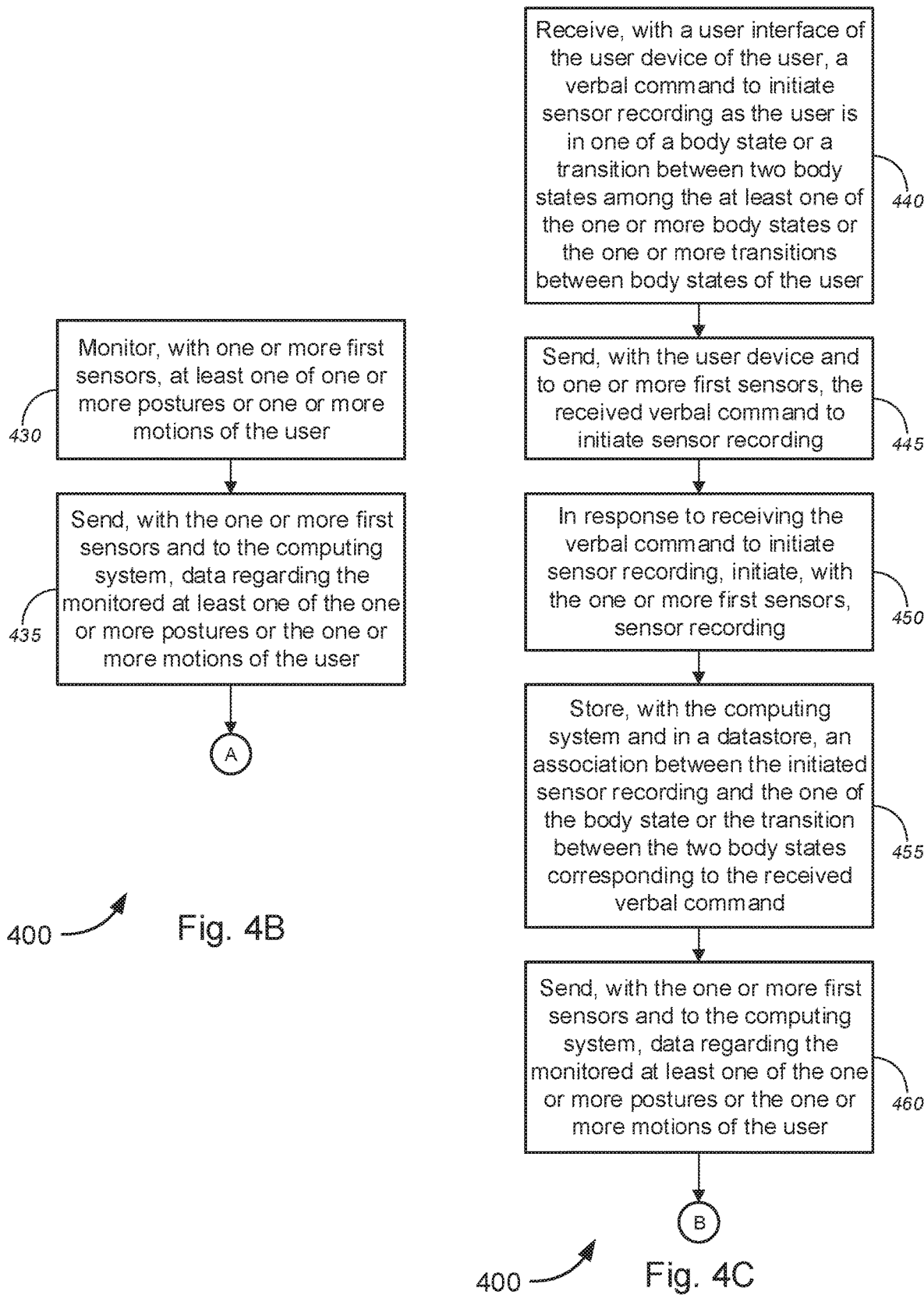

DEVICE-BASED MANEUVER AND ACTIVITY STATE-BASED PHYSIOLOGIC STATUS MONITORING

CROSS-REFERENCES TO RELATED APPLICATIONS

This application claims priority to U.S. Provisional Patent Application Ser. No. 62/785,109, filed Dec. 26, 2018 by Isobel Jane Mulligan et al. (attorney docket no. 0463.18PR), entitled "Method and System for Implementing Device-Based Maneuver and Activity State-Based Physiologic Status Monitoring," the entire disclosure of which is incorporated herein by reference in its entirety for all purposes.

This application may be related to U.S. patent application Ser. No. 15/620,701, filed Jun. 12, 2017 by Mulligan et al. and entitled "Rapid Detection of Bleeding Following Injury", which claims priority to provisional U.S. Patent Application No. 62/349,516, filed Jun. 13, 2016 by Mulligan et al. and entitled "Rapid Detection of Bleeding Following Injury", referred to herein as the "'516 Application"), each of which is incorporated herein by reference in its entirety. This application may also be related to U.S. patent application Ser. No. 15/261,661, filed Sep. 9, 2016 by Mulligan et al. and entitled "Estimating Physiological States Based on Changes in CRI", referred to herein as the "'661 Application"), which claims priority to the '516 Application and to provisional U.S. Patent Application No. 62/216,187, filed Sep. 9, 2015 by Mulligan et al. and entitled "Estimating Physiological States Based on Changes in CRI", referred to herein as the "'187 Application"), each of which is incorporated herein by reference in its entirety.

This application may also be related to U.S. patent application Ser. No. 14/885,891, filed Oct. 16, 2015 by Mulligan et al. and entitled "Assessing Effectiveness of CPR", referred to herein as the "'891 Application") and U.S. patent application Ser. No. 14/885,888, filed Oct. 16, 2015 by Mulligan et al. and entitled "Rapid Detection of Bleeding Before, During, and After Fluid Resuscitation", referred to herein as the "'888 Application"), each of which claims priority to provisional U.S. Patent Application No. 62/064,816, filed Oct. 16, 2014 by Mulligan et al. and titled "Assessing the Effectiveness of CPR", referred to herein as the "'816 Application") and provisional U.S. Patent Application No. 62/064,809 filed Oct. 16, 2014 by Mulligan et al. and titled "Rapid Detection of Bleeding During Fluid Resuscitation"R, referred to herein as the "'809 Application"), each of which is incorporated herein by reference in its entirety.

This application may also be related to U.S. patent application Ser. No. 14/542,426, filed Nov. 14, 2014 by Mulligan et al. and titled, "Noninvasive Hydration Monitoring", referred to herein as the "'426 Application") and U.S. patent application Ser. No. 14/542,423, filed Nov. 14, 2014 by Mulligan et al. and titled, "Noninvasive Monitoring for Fluid Resuscitation" referred to herein as the "'423 Application"), each of which claims priority to provisional U.S. Patent Application No. 61/905,727, filed Nov. 18, 2013 by Mulligan et al. and titled "Noninvasive Hydration Monitoring", referred to herein as the "'727 Application") and provisional U.S. Patent Application No. 61/904,436, filed Nov. 14, 2013 by Mulligan et al. and titled "Noninvasive Monitoring for Fluid Resuscitation", referred to herein as the "'436 Application"), each of which is incorporated herein by reference in its entirety.

This application may also be related to U.S. patent application Ser. No. 14/535,171, filed Nov. 6, 2014 by Mulligan et al. and titled "Noninvasive Predictive and/or Estimative Blood Pressure Monitoring", referred to herein as the "'171 Application"), which claims priority to the '727 Application, the '436 Application, and provisional U.S. Patent Application No. 61/900,980, filed Nov. 6, 2013 by Mulligan et al. and titled "Noninvasive Predictive and/or Estimative Blood Pressure Monitoring", each of which is incorporated herein by reference in its entirety.

This application may also be related to U.S. patent application Ser. No. 13/554,483, filed Jul. 20, 2012 by Grudic et al. and titled, "Hemodynamic Reserve Monitor and Hemodialysis Control", referred to herein as the "'483 Application"; now issued U.S. Pat. No. 9,757,041), which claims priority to provisional U.S. Patent Application No. 61/510,792, filed Jul. 22, 2011 by Grudic et al. and entitled "Cardiovascular Reserve Monitor", referred to herein as the "'792 Application") and provisional U.S. Patent Application No. 61/614,426, filed Mar. 22, 2012 by Grudic et al. and entitled "Hemodynamic Reserve Monitor and Hemodialysis Control", referred to herein as the "'426 Application"), each of which is hereby incorporated by reference in its entirety.

This application may also be related to U.S. patent application Ser. No. 13/041,006, filed Mar. 4, 2011 by Grudic et al. and entitled "Active Physical Perturbations to Enhance Intelligent Medical Monitoring", referred to herein as the "'006 Application"), which claims priority to provisional U.S. Patent Application No. 61/310,583, filed Mar. 4, 2010 by Grudic et al. and titled "Active Physical Perturbations to Enhance Intelligent Medical Monitoring", referred to herein as the "'583 Application"), each of which is hereby incorporated by reference in its entirety.

This application may also be related to U.S. patent application Ser. No. 13/028,140, filed Feb. 15, 2011 by Grudic et al. and entitled "Statistical, Noninvasive Measurement of Intracranial Pressure", referred to herein as the "'140 Application"; now issued U.S. Pat. No. 8,512,260), which claims priority to provisional U.S. Patent Application No. 61/305,110, filed Feb. 16, 2010, by Moulton et al. and titled "Statistical, Noninvasive Method for Predicting Intracranial Pressure", referred to herein as the "'110 Application"), each of which is hereby incorporated by reference in its entirety.

This application may also be related to International Application No. PCT/US2009/062119, filed Oct. 26, 2009 by Grudic et al. and entitled "Long Term Active Learning from Large Continually Changing Data Sets", referred to herein as the "'119 Application"), which claims priority to provisional U.S. Patent Application No. 61/252,978, filed Oct. 19, 2009 by Grudic et al. and titled "Long Term Active Learning from Large Continually Changing Data Sets," provisional U.S. Patent Application No. 61/166,499, filed Apr. 3, 2009 by Moulton and titled "Advances in Pre-Hospital Care," provisional U.S. Patent Application No. 61/166,486, filed Apr. 3, 2009 by Grudic et al. and titled "Statistical Methods for Predicting Patient Specific Blood Loss Volume Causing Hemodynamic Decompensation," provisional U.S. Patent Application No. 61/166,472, filed Apr. 3, 2009 by Grudic et al. and titled "Long Term Active Learning from Large Continually Changing Data Sets," and provisional U.S. Patent Application No. 61/109,490, filed Oct. 29, 2008 by Moulton et al. and titled "Method for Determining Physiological State or Condition," each of which is hereby incorporated by reference in its entirety.

The respective disclosures of these applications/patents (which this document refers to collectively as the "Related Applications") are incorporated herein by reference in their entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to methods, systems, and apparatuses for implementing physiological monitoring, and, more particularly, to methods, systems, and apparatuses for implementing device-based maneuver and activity state-based physiologic status monitoring.

BACKGROUND

With the introduction of portable personal sensors in wearable devices that track or monitor certain physiological characteristics of a person (e.g., pulse or heart rate, step count, etc.), individuals can now roughly gauge their estimated health. Such estimates, however, are extremely rough, and not precise, owing to other unmeasured factors that may break any causal relationships between the pulse or heart rate and/or step count (or other monitored physiological characteristics of an individual and the individual's health.

In particular, most commercially available personal trackers or the like are incapable of accurately determining a hydration state, a dehydration state, a fitness state, a health state (or overall health state), an exertion readiness state, a fatigue state, an alertness level, an altitude sickness state, a level of tolerance to heat, a level of tolerance to cold, a level of tolerance to other environmental conditions, a level of tolerance to liquid limitations, a level of tolerance to blood loss, or one or more states of illness, and/or the like, of an individual, much less that such determination can be performed in real-time or near-real-time and/or that such determination can be made based at least in part on physiological characteristics of the individual that are monitored by the personal trackers.

Hence, there is a need for more robust and scalable solutions for implementing physiological monitoring, and, more particularly, to methods, systems, and apparatuses for implementing device-based maneuver and activity state-based physiologic status monitoring.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

FIGS. 4A-4E are flow diagrams illustrating a method for implementing device-based maneuver and activity state-based physiologic status monitoring, in accordance with various embodiments.

DETAILED DESCRIPTION OF CERTAIN EMBODIMENTS

Overview

Figure 1:
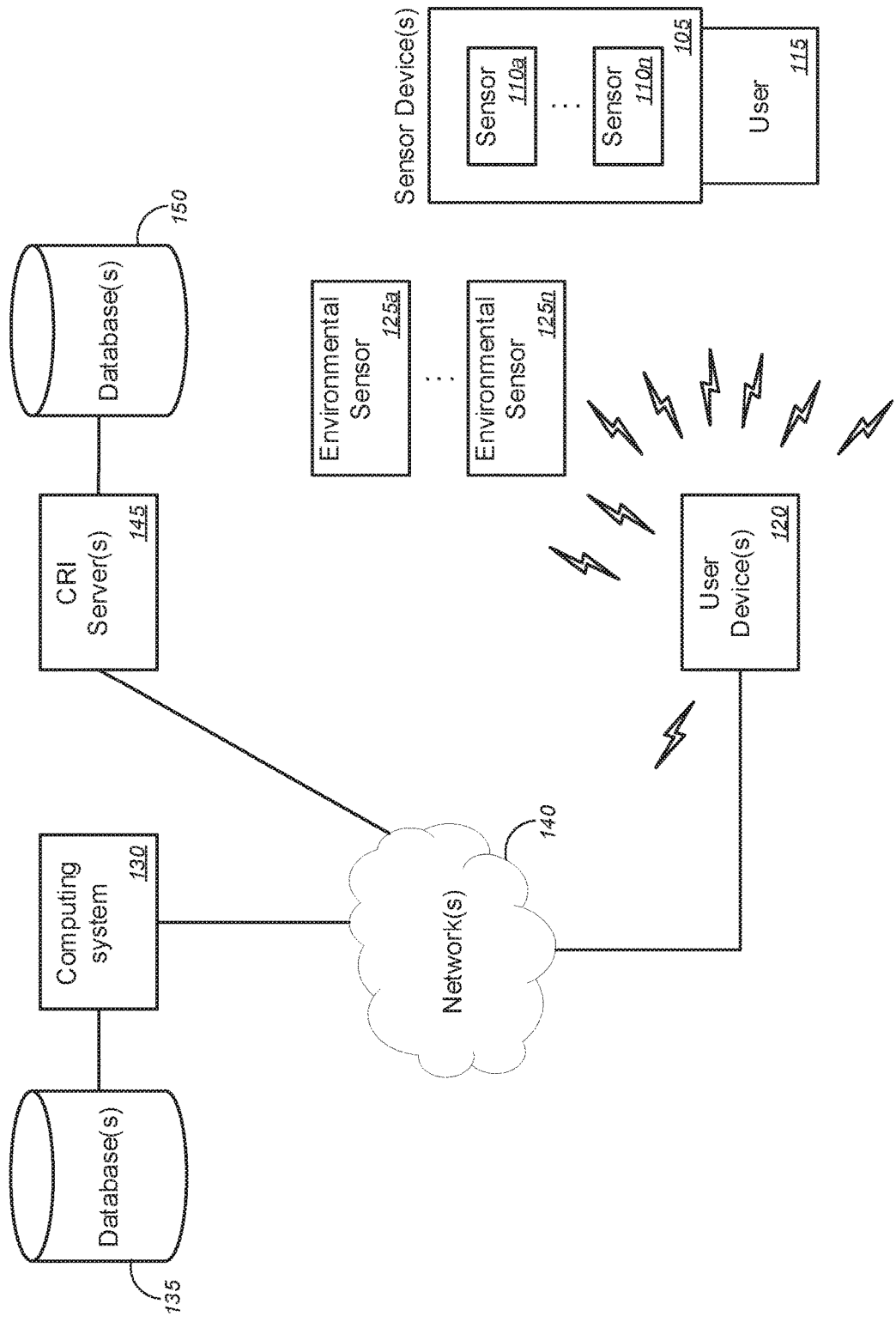
FIG. 1 is a schematic diagram illustrating a system for implementing device-based maneuver and activity state-based physiologic status monitoring, in accordance with various embodiments.

Various embodiments provide tools and techniques for implementing physiological monitoring, and, more particularly, to methods, systems, and apparatuses for implementing device-based maneuver and activity state-based physiologic status monitoring.

In various embodiments, one or more first sensors might monitor at least one of one or more postures or one or more motions, and/or the like, of a user, and might send data regarding the monitored at least one of the one or more postures or the one or more motions, and/or the like, of the user (which might constitute physiological data of the user) to a computing system. In some cases, monitoring, with the one or more first sensors, the at least one of the one or more postures or the one or more motions, and/or the like, of the user might comprise measuring relative positions of two or more of a head of the user, a neck of the user, a shoulder of the user, a chest of the user, a shoulder of the user, an upper arm of the user, an elbow of the user, a wrist of the user, a hand of the user, a finger of the user, a stomach of the user, a hip of the user, a leg of the user, a knee of the user, a calf of the user, an ankle of the user, a foot of the user, or a toe of the user, and/or the like. In some instances, sending the data regarding the monitored at least one of the one or more postures or the one or more motions of the user, and/or the like might comprise sending, with the one or more first sensors and to the computing system, data regarding the monitored at least one of the one or more postures or the one or more motions of the user, and/or the like, via wireless communications.

Alternatively, or additionally, the user might utilize a user interface of a user device (which may be associated with the user) to issue or otherwise speak a verbal command to initiate sensor recording as the user is in one of a body state or a transition between two body states among the at least one of the one or more body states or the one or more transitions between body states, and/or the like, of the user. The user device might then send the received verbal command to the one or more first sensors to initiate sensor recording. In response to receiving the verbal command to initiate sensor recording, the one or more first sensors might initiate sensor recording to monitor at least one of one or more postures, one or more motions, and/or the like, of the user. The computing system might subsequently or concurrently store in a datastore an association between the initiated sensor recording and the one of the body state or the transition between the two body states, and/or the like, corresponding to the received verbal command. The one or more first sensors might subsequently send to the computing system data regarding the monitored at least one of the one or more postures or the one or more motions, and/or the like, of the user, where the physiological data of the user might include, but is not limited to, the data regarding the monitored at least one of the one or more postures or the one or more motions of the user and data regarding the association between the initiated sensor recording and the one of the body state or the transition between the two body states, and/or the like, corresponding to the received verbal command.

Alternatively, or additionally, the one or more first sensors might monitor the physiological state of the user, including, but not limited to, at least one of skin temperature, moisture, resistance, electrodermal activity ("EDA"), body temperature, core temperature, fluid intake amount, CRI, hemodynamic status, closeness of hemodynamic collapse due to at least one of heat stress, hydration, and/or central fluid loss, one or more pulsatile components of a cardiac cycle, electrical activity of the heart, respiration rate, blood pressure, and/or the like. Concurrently, one or more environmental sensors might monitor one or more ambient environmental conditions (near or around the user; particularly, as the physiological state of the user is being monitored), the one or more ambient environmental conditions including, without limitation, one of moisture, humidity, rainfall, temperature, atmospheric pressure, air quality, windspeed, windchill, or altitude, and/or the like.

In some aspects, the computing system might receive physiological data of the user—which might include, without limitation, data sent by the one or more first sensors; data regarding the association between the initiated sensor recording and the one of the body state or the transition between the two body states, corresponding to the received verbal command; or the data regarding the ambient environmental conditions sent by the sensors; and/or the like. The computing system might analyze the received physiological data of the user to identify at least one of one or more body states or one or more transitions between body states of the user—that is, one of a face-up prone state of the user, a face-down prone state of the user, a sitting state of the user, a standing state of the user, a planking state of the user, a squatting state of the user, a walking state of the user, a running state of the user, a jumping state of the user, or an exercise state of the user, and/or the like, or one or more transitions between two of these body states. The computing system might determine at least one physiological state of the user, based at least in part on an analysis of the identified at least one of the one or more body states or the one or more transitions between body states of the user (or based at least in part on one or more of the analysis of the identified at least one of the one or more body states or the one or more transitions between body states of the user, an analysis of the monitored physiological state of the user, or an analysis of the monitored one or more ambient environmental conditions, and/or the like).

Merely by way of example, in some cases, the at least one physiological state of the user might include, without limitation, at least one of a hydration state of the user, a dehydration state of the user, a fitness state of the user, a health state of the user, an exertion readiness state of the user, a fatigue state of the user, an alertness level of the user, an altitude sickness state of the user, a level of tolerance to heat of the user, a level of tolerance to cold of the user, a level of tolerance to other environmental conditions of the user, a level of tolerance to liquid limitations of the user, a level of tolerance to blood loss of the user, or one or more states of illness of the user (including, but not limited to, flu, cold, viral infection, bacterial infection, sepsis, heart disease, and/or the like), and/or the like.

The computing system might then send the determined at least one physiological state of the user to the user device(s) of the user for display on a display screen of the user device(s).

According to some aspects, a measurement of compensatory reserve, as characterized by a compensatory reserve index (which is described in detail in the Related Applications, which have already been incorporated herein by reference in their entirety for all purposes), may be indicative of a body state of the user. In particular, the inventors of this application have found that physical activity or a change in physical activity of the user (e.g., a body state (as described herein) or a transition between body states (as also described herein)) may result in an impulse response in the CRI of the user. Profiles of the CRI (as compared with base measurements of CRI of the individual user or a compilation of measurements of CRI across a sample of multiple users) may be indicative of health, fitness, and/or other physiological states of the user. In such cases, a CRI server or other computational device might monitor physiological data of the user (e.g., by using sensors, including, but not limited to the one or more first sensors, as described herein) to measure a CRI of the user, and might further analyze the measured CRI to determine a body state of the user and/or a transition between body states of the user, and might also further analyze the measured CRI to determine the physiological state of the user—including, but not limited to, at least one of a hydration state of the user, a dehydration state of the user, a fitness state of the user, a health state of the user, an exertion readiness state of the user, a fatigue state of the user, an alertness level of the user, an altitude sickness state of the user, a level of tolerance to heat of the user, a level of tolerance to cold of the user, a level of tolerance to other environmental conditions of the user, a level of tolerance to liquid limitations of the user, a level of tolerance to blood loss of the user, or one or more states of illness of the user (including, but not limited to, flu, cold, viral infection, bacterial infection, sepsis, heart disease, and/or the like), and/or the like. Such physiological states may then be presented to the user (or a physician or other healthcare provider of the user) using a user interface of a user device, a display screen of a user device, a web portal, a software application ("app"), and/or the like.

In some embodiments, the physiological state determination may be performed in real-time or near-real-time based on the monitored sensor data (i.e., physiological data collected or monitored by the one or more first sensors).

In some aspects, the method and system of the various embodiments might allow for a portable device or system to monitor maneuver (or motion) and activity of a user to (accurately and/or precisely) determine a physiological state of the user based on maneuvers (or motions) and states of the user that are either automatically detected by the portable device or system and/or annotated by the user. These physiological states of the user may be reflected, in some cases, in changes to measured CRI of the user (where measurement of CRI in general has been described in detail in the Related Applications, which have already been incorporated herein by reference in their entirety for all purposes), thereby providing real-time or near-real-time assessments of the health, fitness, or other physiological states of the user based at least in part on monitored physiological data of the user (and, in some cases, based at least in part on measured CRI of the user).

These and other aspects of the device-based maneuver and activity state-based physiologic status monitoring are described in greater detail with respect to the figures.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Various embodiments described herein, while embodying (in some cases) software products, computer-performed methods, and/or computer systems, represent tangible, concrete improvements to existing technological areas, including, without limitation, personal tracking technology, health monitoring technology, and/or the like. In other aspects, certain embodiments, can improve the functioning of user equipment or systems themselves (e.g., personal trackers, portable health monitors, etc.), for example, by receiving, with a computing system, physiological data of a user; analyzing, with the computing system, the received physiological data of the user to identify at least one of one or more body states or one or more transitions between body states of the user; determining, with the computing system, at least one physiological state of the user, based at least in part on an analysis of the identified at least one of the one or more body states or the one or more transitions between body states of the user; sending, with the computing system and to a user device (e.g., a user device of the user, a user device of a physician or other healthcare provider of the user, etc.), the determined at least one physiological state of the user; and displaying, on a display screen of the user device, the determined at least one physiological state of the user; and/or the like.

In particular, to the extent any abstract concepts are present in the various embodiments, those concepts can be implemented as described herein by devices, software, systems, and methods that involve specific novel functionality (e.g., steps or operations), such as, allowing for a portable device or system to monitor maneuver (or motion) and activity of a user to (accurately and/or precisely) determine a physiological state of the user based on maneuvers (or motions) and states of the user that are either automatically detected by the portable device or system and/or annotated by the user. These physiological states of the user may be reflected, in some cases, in changes to measured CRI of the user (where measurement of CRI in general has been described in detail in the Related Applications, which have already been incorporated herein by reference in their entirety for all purposes), thereby providing real-time or near-real-time assessments of the health, fitness, or other physiological states of the user based at least in part on monitored physiological data of the user (and, in some cases, based at least in part on measured CRI of the user), which produce tangible results outside of the implementing computer system.

In an aspect, a method might comprise receiving, with a computing system, physiological data of a user; analyzing, with the computing system, the received physiological data of the user to identify at least one of one or more body states or one or more transitions between body states of the user; and determining, with the computing system, at least one physiological state of the user, based at least in part on an analysis of the identified at least one of the one or more body states or the one or more transitions between body states of the user. The method might further comprise sending, with the computing system and to a user device, the determined at least one physiological state of the user; and displaying, on a display screen of the user device, the determined at least one physiological state of the user.

In some embodiments, the method might further comprise monitoring, with one or more first sensors, at least one of one or more postures or one or more motions of the user; and sending, with the one or more first sensors and to the computing system, data regarding the monitored at least one of the one or more postures or the one or more motions of the user, wherein the physiological data of the user might comprise the data regarding the monitored at least one of the one or more postures or the one or more motions of the user.

In some cases, the one or more first sensors might comprise at least one of one or more accelerometers, one or more gyroscopes, one or more location sensors, one or more pedometers, one or more compasses, or one or more altimeters, and/or the like. Alternatively, or additionally, the one or more first sensors are each encapsulated within a sensor device, wherein each sensor device might comprise one of a patch-based sensor device, a wrist strap-based sensor device, an arm strap-based sensor device, a head band-based sensor device, a belt-based sensor device, a leg strap-based sensor device, an ankle strap-based sensor device, or a shoe strap-based sensor device, and/or the like.

According to some embodiments, monitoring, with one or more first sensors, the at least one of the one or more postures or the one or more motions of the user might comprise measuring relative positions of two or more of a head of the user, a neck of the user, a shoulder of the user, a chest of the user, a shoulder of the user, an upper arm of the user, an elbow of the user, a wrist of the user, a hand of the user, a finger of the user, a stomach of the user, a hip of the user, a leg of the user, a knee of the user, a calf of the user, an ankle of the user, a foot of the user, or a toe of the user, and/or the like. In some instances, sending the data regarding the monitored at least one of the one or more postures or the one or more motions of the user might comprise sending, with the one or more first sensors and to the computing system, data regarding the monitored at least one of the one or more postures or the one or more motions of the user, via wireless communications.

Alternatively, the method might further comprise receiving, with a user interface of the user device, a verbal command to initiate sensor recording as the user is in one of a body state or a transition between two body states among the at least one of the one or more body states or the one or more transitions between body states of the user; sending, with the user device and to one or more first sensors, the received verbal command to initiate sensor recording; in response to receiving the verbal command to initiate sensor recording, initiating, with the one or more first sensors, sensor recording to monitor at least one of one or more postures or one or more motions of the user; storing, with the computing system and in a datastore, an association between the initiated sensor recording and the one of the body state or the transition between the two body states corresponding to the received verbal command; and sending, with the one or more first sensors and to the computing system, data regarding the monitored at least one of the one or more postures or the one or more motions of the user, wherein the physiological data of the user might comprise the data regarding the monitored at least one of the one or more postures or the one or more motions of the user and data regarding the association between the initiated sensor recording and the one of the body state or the transition between the two body states corresponding to the received verbal command.

Alternatively, or additionally, the method might further comprise monitoring, with one or more second sensors, physiological state of the user; monitoring, with one or more third sensors, one or more ambient environmental conditions; receiving, with the computing system, the monitored physiological state of the user; and receiving, with the computing system, the monitored one or more ambient environmental conditions. In some embodiments, the one or more second sensors might each comprise one of one or more skin temperature sensors; one or more moisture sensors; one or more resistance sensors; one or more electrodermal activity ("EDA") sensors; one or more body temperature sensors; one or more core temperature sensors; one or more fluid intake measurement sensors; one or more sensors measuring a compensatory reserve index ("CRI") of the user; one or more sensors measuring hemodynamic status of the user; one or more sensors measuring closeness of hemodynamic collapse due to at least one of heat stress, hydration, or central fluid loss; one or more sensors that continuously capture one or more pulsatile components of a cardiac cycle of the user; one or more electrocardiograph sensors; or one or more respiration rate sensors; and/or the like. In some cases, the one or more sensors that continuously capture the one or more pulsatile components of the cardiac cycle of the user might comprise at least one of radio frequency ("RF") sensor, a photoplethysmograph ("PPG"), a volume clamp, or a continuous blood pressure ("BP") sensor, and/or the like. According to some embodiments, the one or more ambient environmental conditions might each comprise one of moisture, humidity, rainfall, temperature, atmospheric pressure, air quality, windspeed, windchill, or altitude, and/or the like.

In some instances, determining, with the computing system, the at least one physiological state of the user might comprise determining, with the computing system, at least one physiological state of the user, based at least in part on one or more of the analysis of the identified at least one of the one or more body states or the one or more transitions between body states of the user, an analysis of the monitored physiological state of the user, or an analysis of the monitored one or more ambient environmental conditions.

Merely by way of example, in some cases, the one or more body states might each comprise one of a face-up prone state of the user, a face-down prone state of the user, a sitting state of the user, a standing state of the user, a planking state of the user, a squatting state of the user, a walking state of the user, a running state of the user, a jumping state of the user, or an exercise state of the user, and/or the like. The one or more transitions between body states of the user might each comprise transitions between two of said one or more body states. In some embodiments, the at least one physiological state of the user might comprise at least one of a hydration state of the user, a dehydration state of the user, a fitness state of the user, a health state of the user, an exertion readiness state of the user, a fatigue state of the user, an alertness level of the user, an altitude sickness state of the user, a level of tolerance to heat of the user, a level of tolerance to cold of the user, a level of tolerance to other environmental conditions of the user, a level of tolerance to liquid limitations of the user, a level of tolerance to blood loss of the user, or one or more states of illness of the user (including, but not limited to, flu, cold, viral infection, bacterial infection, sepsis, heart disease, and/or the like), and/or the like. In some instances, the user device might comprise one of a smart phone, a mobile phone, a smart watch, a tablet computer, a laptop computer, a desktop computer, or a dedicated sensor control device, and/or the like.

In another aspect, an apparatus might comprise at least one processor and a non-transitory computer readable medium communicatively coupled to the at least one processor. The non-transitory computer readable medium might have stored thereon computer software comprising a set of instructions that, when executed by the at least one processor, causes the apparatus to: receive physiological data of a user; analyze the received physiological data of the user to identify at least one of one or more body states or one or more transitions between body states of the user; determine at least one physiological state of the user, based at least in part on an analysis of the identified at least one of the one or more body states or the one or more transitions between body states of the user; send, to a user device, the determined at least one physiological state of the user; and display, on a display screen of the user device, the determined at least one physiological state of the user.

In yet another aspect, a system might comprise a computing system, which might comprise at least one first processor and a first non-transitory computer readable medium communicatively coupled to the at least one first processor. The first non-transitory computer readable medium might have stored thereon computer software comprising a first set of instructions that, when executed by the at least one first processor, causes the computing system to: receive physiological data of a user; analyze the received physiological data of the user to identify at least one of one or more body states or one or more transitions between body states of the user; determine at least one physiological state of the user, based at least in part on an analysis of the identified at least one of the one or more body states or the one or more transitions between body states of the user; send, to a user device, the determined at least one physiological state of the user; and display, on a display screen of the user device, the determined at least one physiological state of the user.

According to some embodiments, the system might further comprise one or more first sensors, wherein the one or more first sensors are used to monitor at least one of one or more postures or one or more motions of the user, wherein the one or more first sensors send, to the computing system, data regarding the monitored at least one of the one or more postures or the one or more motions of the user, wherein the physiological data of the user might comprise the data regarding the monitored at least one of the one or more postures or the one or more motions of the user. In some cases, the one or more first sensors might comprise at least one of one or more accelerometers, one or more gyroscopes, one or more location sensors, one or more pedometers, one or more compasses, or one or more altimeters, and/or the like. Alternatively, or additionally, the one or more first sensors are each encapsulated within a sensor device, wherein each sensor device might comprise one of a patch-based sensor device, a wrist strap-based sensor device, an arm strap-based sensor device, a head band-based sensor device, a belt-based sensor device, a leg strap-based sensor device, an ankle strap-based sensor device, or a shoe strap-based sensor device, and/or the like.

In some embodiments, monitoring, with one or more first sensors, the at least one of the one or more postures or the one or more motions of the user might comprise measuring relative positions of two or more of a head of the user, a neck of the user, a shoulder of the user, a chest of the user, a shoulder of the user, an upper arm of the user, an elbow of the user, a wrist of the user, a hand of the user, a finger of the user, a stomach of the user, a hip of the user, a leg of the user, a knee of the user, a calf of the user, an ankle of the user, a foot of the user, or a toe of the user, and/or the like. In some instances, sending the data regarding the monitored at least one of the one or more postures or the one or more motions of the user might comprise sending, with the one or more first sensors and to the computing system, data regarding the monitored at least one of the one or more postures or the one or more motions of the user, via wireless communications.

According to some embodiments, the system might further comprise the user device, which might comprise a user interface, at least one second processor, and a second non-transitory computer readable medium communicatively coupled to the at least one second processor. The second non-transitory computer readable medium might have stored thereon computer software comprising a second set of instructions that, when executed by the at least one second processor, causes the user device to: receive, with the user interface, a verbal command to initiate sensor recording as the user is in one of a body state or a transition between two body states among the at least one of the one or more body states or the one or more transitions between body states of the user; and send, to the one or more first sensors, the received verbal command to initiate sensor recording, wherein, in response to receiving the verbal command to initiate sensor recording, the one or more first sensors initiates sensor recording to monitor at least one of one or more postures or one or more motions of the user. The first set of instructions, when executed by the at least one first processor, might further cause the computing system to: store, in a datastore, an association between the initiated sensor recording and the one of the body state or the transition between the two body states corresponding to the received verbal command. The one or more first sensors might send, to the computing system, data regarding the monitored at least one of the one or more postures or the one or more motions of the user, wherein the physiological data of the user might comprise the data regarding the monitored at least one of the one or more postures or the one or more motions of the user and data regarding the association between the initiated sensor recording and the one of the body state or the transition between the two body states corresponding to the received verbal command.

The system might further comprise one or more second sensors and one or more third sensors. The one or more second sensors might monitor physiological state of the user, wherein the one or more second sensors might each comprise one of one or more skin temperature sensors; one or more moisture sensors; one or more resistance sensors; one or more electrodermal activity ("EDA") sensors; one or more body temperature sensors; one or more core temperature sensors; one or more fluid intake measurement sensors; one or more sensors measuring a compensatory reserve index ("CRI") of the user; one or more sensors measuring hemodynamic status of the user; one or more sensors measuring closeness of hemodynamic collapse due to at least one of heat stress, hydration, or central fluid loss; one or more sensors that continuously capture one or more pulsatile components of a cardiac cycle of the user; one or more electrocardiograph sensors; or one or more respiration rate sensors; and/or the like. The one or more sensors that continuously capture the one or more pulsatile components of the cardiac cycle of the user might comprise at least one of radio frequency ("RF") sensor, a photoplethysmograph ("PPG"), a volume clamp, or a continuous blood pressure ("BP") sensor, and/or the like. The one or more third sensors might monitor one or more ambient environmental conditions, wherein the one or more ambient environmental conditions might each comprise one of moisture, humidity, rainfall, temperature, atmospheric pressure, air quality, windspeed, windchill, or altitude, and/or the like.

The first set of instructions, when executed by the at least one first processor, might further cause the computing system to: receive the monitored physiological state of the user; and receive the monitored one or more ambient environmental conditions. In some cases, determining the at least one physiological state of the user might comprise determining at least one physiological state of the user, based at least in part on one or more of the analysis of the identified at least one of the one or more body states or the one or more transitions between body states of the user, an analysis of the monitored physiological state of the user, or an analysis of the monitored one or more ambient environmental conditions, or the like.

Merely by way of example, in some instances, the user device might comprise one of a smart phone, a mobile phone, a smart watch, a tablet computer, a laptop computer, a desktop computer, or a dedicated sensor control device, and/or the like.

Various modifications and additions can be made to the embodiments discussed without departing from the scope of the invention. For example, while the embodiments described above refer to particular features, the scope of this invention also includes embodiments having different combination of features and embodiments that do not include all of the above described features.

Compensatory Reserve Index ("CRI")

Various embodiments can assess the effectiveness of fluid intake hydration, where effectiveness can be defined as, but not limited to, leading to a better hydration state or maintain an optimal hydration state. In one aspect, optimal hydration might be defined as a fluid state that maximized some performance index/measure, perhaps indicated by the patient's compensatory reserve index ("CRI," also referred to herein and in the Related Applications as "cardiac reserve index" or "hemodynamic reserve index" ("HDRI"), all of which should be considered synonymous for purposes of this disclosure). (While the term, "patient," is used herein for convenience, that descriptor should not be considered limiting, because various embodiments can be employed both in a clinical setting and outside any clinical setting, such as by an athlete before, during, or after an athletic contest or training, a person during daily activities, a soldier on the battlefield, etc. Thus, the term, "patient," as used herein, should be interpreted broadly and should be considered to be synonymous with "person.") In other cases, the assessments might be based on raw waveform data (e.g., PPG waveform data) captured by a sensor on the patient (such as the sensors described below and the Related Applications, for example). In further cases, a combination of waveform data and calculated/estimated CRI can be used to calculate the effectiveness of hydration and/or the amount of fluid needed for effective hydration. In other aspects, such functionality can be provided by and/or integrated with systems, devices (such as a cardiac reserve monitor and/or wrist-worn sensor device, or the like), tools, techniques, methods, and software described below and in the Related Applications.

For example, one set of embodiments provides methods. An exemplary method might comprise monitoring, with one or more sensors, physiological data of a patient. The method might further comprise analyzing, with a computer system, the physiological data. Many different types of physiological data can be monitored and/or analyzed by various embodiments, including, without limitation, blood pressure waveform data, plethysmograph waveform data, photoplethysmograph ("PPG") waveform data (such as that generated by a pulse oximeter), and/or the like. In an aspect of some embodiments, analyzing the physiological data might comprise analyzing the data against a pre-existing model. In some cases, the method can further comprise assessing the effectiveness of hydration efforts, and/or displaying (e.g., on a display device) an assessment of the effectiveness of the hydration efforts. Such an assessment can include, without limitation, an estimate of the effectiveness at a current time, a prediction of the effectiveness at some point in the future, an estimate and/or prediction of a volume of fluid necessary for effective hydration, an estimate of the probability a patient requires fluids, etc.

An apparatus, in accordance with yet another set of embodiments, might comprise a computer readable medium having encoded thereon a set of instructions executable by one or more computers to perform one or more operations. In some embodiments, the set of instructions might comprise instructions for performing some or all of the operations of methods provided by certain embodiments.

A system, in accordance with yet another set of embodiments, might comprise one or more processors and a computer readable medium in communication with the one or more processors. The computer readable medium might have encoded thereon a set of instructions executable by the computer system to perform one or more operations, such as the set of instructions described above, to name one example. In some embodiments, the system might further comprise one or more sensors and/or a therapeutic device, either or both of which might be in communication with the processor and/or might be controlled by the processor. Such sensors can include, but are not limited to, a blood pressure sensor, an intracranial pressure monitor, a central venous pressure monitoring catheter, an arterial catheter, an electroencephalograph, a cardiac monitor, a transcranial Doppler sensor, a transthoracic impedance plethysmograph, a pulse oximeter, a near infrared spectrometer, a ventilator, an accelerometer, an electrooculogram, a transcutaneous glucometer, an electrolyte sensor, and/or an electronic stethoscope.

CRI for Determining Body States, Transition Between Body States, and Physiological States of User The inventors of this application have found that physical activity or a change in physical activity of the user (e.g., a body state (as described herein) or a transition between body states (as also described herein)) may result in an impulse response in the CRI of the user. Profiles of the CRI (as compared with base measurements of CRI of the individual user or a compilation of measurements of CRI across a sample of multiple users) may be indicative of health, fitness, and/or other physiological states of the user. In such cases, a CRI server or other computational device might monitor physiological data of the user (e.g., by using sensors, including, but not limited to the one or more first sensors, as described herein) to measure a CRI of the user, and might further analyze the measured CRI to determine a body state of the user and/or a transition between body states of the user, and might also further analyze the measured CRI to determine the physiological state of the user—including, but not limited to, at least one of a hydration state of the user, a dehydration state of the user, a fitness state of the user, a health state of the user, an exertion readiness state of the user, a fatigue state of the user, an alertness level of the user, an altitude sickness state of the user, a level of tolerance to heat of the user, a level of tolerance to cold of the user, a level of tolerance to other environmental conditions of the user, a level of tolerance to liquid limitations of the user, a level of tolerance to blood loss of the user, or one or more states of illness of the user (including, but not limited to, flu, cold, viral infection, bacterial infection, sepsis, heart disease, and/or the like), and/or the like. Such physiological states may then be presented to the user (or a physician or other healthcare provider of the user) using a user interface of a user device, a display screen of a user device, a web portal, a software application ("app"), and/or the like. These functionalities are described in detail herein below.

CRI for Assessing Blood Loss

A set of embodiments provides methods, systems, and software that can be used, in many cases noninvasively, to quickly and accurately assess blood loss in a patient (e.g., before, during, and/or after fluid resuscitation). Such an assessment can include, without limitation, an estimate of the effectiveness at a current time, a prediction of the effectiveness at some point in the future, an estimate and/or prediction of a volume of fluid necessary for effective hydration, an estimate of the probability a patient requires fluids, an estimate and/or prediction of blood loss (e.g., before, during, and/or after fluid resuscitation), etc. In a particular set of embodiments, a device, which can be worn on the patient's body, can include one or more sensors that monitor a patient's physiological parameters. The device (or a computer in communication with the device) can analyze the data captured by the sensors and compare such data with a model (which can be generated in accordance with other embodiments) to assess the effectiveness of hydration, as described in further detail in the '426 Application, and/or to assess blood loss (e.g., before, during, and/or after fluid resuscitation).

Different embodiments can measure a number of different physiological parameters from the patient, and the analysis of those parameters can vary according to which parameters are measured (and which, according to the generated model, are found to be most predictive of the effectiveness of hydration, including the probability of the need for hydration and/or the volume of fluids needed, or most predictive of blood loss). In some cases, the parameters themselves (e.g., continuous waveform data captured by a photoplethysmograph) can be analyzed against the model to make assessments of hydration effectiveness or assessments of blood loss (e.g., before, during, and/or after fluid resuscitation). In other cases, physiological parameters can be derived from the captured data, and these parameters can be used Merely by way of example, as described further below and the '483 Application (already incorporated by reference), direct physiological data (captured by sensors) can be used to estimate a value of CRI, and this value of CRI can be used to assess the effectiveness of hydration and/or to assess blood loss (e.g., before, during, and/or after fluid resuscitation). In yet other cases, the derived CRI values and raw sensor data can be used together to perform such assessments.

For example, the '483 Application describes a compensatory reserve monitor (also described as a cardiac reserve monitor or hemodynamic reserve monitor) that is able to estimate the compensatory reserve of a patient. In an aspect, this monitor quickly, accurately, and/or in real-time can determine the probability of whether a patient is bleeding. In another aspect, the device can simultaneously monitor the patient's compensatory reserve by tracking the patient's CRI, to appropriately and effectively guide hydration and ongoing patient care. The same device (or a similar device) can also include advanced functionality to assess the effectiveness of hydration, based on the monitored CRI values, as explained in further detail in the '426 Application, and/or to rapidly assess blood loss (e.g., before, during, and/or after fluid resuscitation).

CRI is a hemodynamic parameter that is indicative of the individual-specific proportion of intravascular fluid reserve remaining before the onset of hemodynamic decompensation. CRI has values that range from 1 to 0, where values near 1 are associated with normovolemia (normal circulatory volume) and values near 0 are associated with the individual specific circulatory volume at which hemodynamic decompensation occurs.

The mathematical formula of CRI, at some time "t" is given by the following equation:

$$CRI(t) = 1 - \frac{BLV(t)}{BLV_{HDD}} \qquad (Eq. 1)$$

where BLV(t) is the intravascular volume loss ("BLV," also referred to as "blood loss volume" in the Related Applications) of a person at time "t," and $BLV_{HDD}$ is the intravascular volume loss of a person when they enter hemodynamic decompensation ("HDD"). Hemodynamic decompensation is generally defined as occurring when the systolic blood pressure falls below 70 mmHg. This level of intravascular volume loss is individual specific and will vary from subject to subject.

Lower body negative pressure ("LBNP") in some linear or nonlinear relationship λ with intravascular volume loss:

$$BLV = \lambda \cdot LBNP \qquad (Eq. 2)$$

can be used in order to estimate the CRI for an individual undergoing a LBNP experiment as follows:

$$CRI = 1 - \frac{BLV(t)}{BLV_{HDD}} \approx 1 - \frac{\lambda \cdot LBNP(t)}{\lambda \cdot LBNP_{HDD}} = 1 - \frac{LBNP(t)}{LBNP_{HDD}} \qquad (Eq. 3)$$

where LBNP(t) is the LBNP level that the individual is experiencing at time "t," and, $LBNP_{HDD}$ is the LNPB level that the individual will enter hemodynamic decompensation.

Using either CRI data, raw (or otherwise processed) sensor data, or both, various embodiments can assess the effectiveness of hydration. In one embodiment, the assessment of blood loss ("BL") can be expressed as a value between 0 and 1; when BL=1, blood loss is certain, when BL=0, there is no blood loss, and when BL is a value between 1 and 0, the value is indicative of probability of blood loss, perhaps due to ongoing bleeding before, during, and/or after fluid resuscitation. (Of course, other embodiments can scale the value of BL differently). In an aspect of some embodiments, a general expression for the estimate of blood loss is as follows:

$$BL = f_{BL}(CRI_t, FV_t, S_t) \qquad (Eq. 4)$$

where BL is a measure or an estimate of blood loss, $f_{BL}(CRI_t, FV_t, S_t)$ is an algorithm embodied by a model generated empirically, e.g., using the techniques described with respect to FIG. 4 below, and/or in the Related Applications, $CRI_t$ is a time history of CRI values (which can range from a single CRI value to many hours of CRI values), $FV_t$ is a time history of fluid volume being given to the patient (which can range from a single value to many hours of values), and $S_t$ is a time history of raw sensor values, such as physiological data measured by the sensors, as described elsewhere herein (which can range from one value to many hours of values).

The functional form of Eq. 4 is similar to but not limited to the form of the CRI model in the sense that time histories of ($CRI_t, FV_t, S_t$) data gathered from human subjects at various levels of BL are compared to time histories of ($CRI_t, FV_t, S_t$) for the current patient being monitored. The estimated BL for the current patient is then that which is the closest in ($CRI_t, FV_t, S_t$) space to the previously gathered data.

While Eq. 4 is the general expression for BL, various embodiments might use subsets of the parameters considered in Eq. 4. For instance, in one embodiment, a model might consider only the volume of fluid and CRI data, without accounting for raw sensor input. In that case, BL can be calculated as follows:

$$BL = f_{BL}(CRI_t, FV_t). \qquad (Eq. 5)$$

Similarly, some models might estimate BL based on sensor data, rather than first estimating CRI, in which case, BL can be expressed thusly:

$$BL = f_{BL}(FV_t, S_t). \qquad (Eq. 6)$$

The choice of parameters to use in modeling BL is discretionary, and it can depend on what parameters are shown (e.g., using the techniques of FIG. 4, below) to result in the best prediction of BL.

In another aspect, the effectiveness of hydration can be assessed by estimating or predicting the volume, V, of fluid necessary for effective hydration of the patient. This volume, V, can indicate a volume of fluid needed for full hydration if therapy has not yet begun, and/or it can indicate a volume remaining for fully effective hydration if therapy is underway. Like BL, the value of V can be estimated/predicted using the modeling techniques described herein and in the Related Applications. In a general case, V can be expressed as the following:

$$V = f_V(CRI_t, FV_t, S_t) \qquad (Eq. 7)$$

where V is an estimated volume of fluid needed by a patient need to prevent over or under hydration, $f_v(CRI_t, FV_t, S_t)$ is an algorithm embodied by a model generated empirically, e.g., using the techniques described with respect to FIG. 4 below, and/or in the Related Applications, $CRI_t$ is a time history of CRI values, $FV_t$ is a time history of fluid volume being given to the patient, and $S_t$ is a time history of physiological data received from the one or more sensors.

As with the estimate of BL, various embodiments can employ subsets of the parameters used in the general expression of Eq. 7. Thus, different embodiments might calculate V as follows:

$$V = f_v(CRI_t, FV_t) \quad (Eq. 8)$$

or $$V = f_v(FV_t, S_t) \quad (Eq. 9)$$

Yet another way of assessing effectiveness of hydration (which can even include assessing the need for hydration) is estimating the probability $P_f$ that the patient requires fluids; this probability can estimate the likelihood that the patient requires hydration if therapy has not been initiated, and/or, if hydration therapy is underway, the probability can estimate the likelihood that further hydration is necessary. The value of this probability, which can be expressed, e.g., as a percentage, as a decimal value between 0 and 1, etc. can be estimated using the following expression:

$$P_f = f_{Pf}(CRI_t, S_t) \quad (Eq. 10)$$

where $P_f$ is the estimated probability that the patient requires fluid, $f_{Pf}(CRI_t, S_t)$ is a relationship derived based on empirical study, $CRI_t$ is a time history of CRI values, and $S_t$ is a time history of physiological data received from the one or more sensors. Once again, this general expression can be employed, in various embodiments, using subsets of the parameters in the general expression, such as the following:

$$P_f = f_{Pf}(CRI_t) \quad (Eq. 11)$$

or $$P_f = f_{Pf}(S_t) \quad (Eq. 12)$$

In the estimate of any of BL, V, or $P_f$, the function $f$ expresses a relationship that is derived based on empirical study. In a set of embodiments, for example, various sensor data can be collected from test subjects before, during, and/or after hydration efforts, during hemorrhaging, or under other conditions that might simulate such situations. This sensor data can be analyzed to develop models, using techniques similar to those of FIG. 4 below, which can then be used to estimate various assessments of hydration effectiveness, using, e.g., the methods described below with respect to FIGS. 2 and 3.

A measure of CRI, BL, V, and/or $P_f$ can be useful in a variety of clinical settings, including, but not limited to: 1) acute blood loss volume due to injury or surgery; 2) acute circulatory volume loss due to hemodialysis (also called intradialytic hypotension); and 3) acute circulatory volume loss due to various causes of dehydration (e.g., reduced fluid intake, vomiting, dehydration, etc.). A change in CRI can also herald other conditions, including, without limitation, changes in blood pressure, general fatigue, overheating, and/or certain types of illnesses. Accordingly, the tools and techniques for estimating and/or predicting CRI can have a variety of applications in a clinical setting, including, without limitation, diagnosing such conditions.

Moreover, measures of CRI, BL, V, and/or $P_f$ can have applicability outside the clinical setting. For example, an athlete can be monitored (e.g., using a wrist-wearable hydration monitor) before, during, or after competition or training to ensure optimal performance (and overall health and recovery). In other situations, a person concerned about overall wellbeing can employ a similar hydration monitor to ensure that he or she is getting enough (but not too much) fluid, ill infants or adults can be monitored while ill to ensure that symptoms (e.g., vomiting, diarrhea, etc.) do not result in dehydration, and the like. Similarly, soldiers in the field (particularly in harsh conditions) can be monitored to ensure optimal operational readiness.

In various embodiments, a hydration monitor, compensatory reserve monitor, a wrist-wearable sensor device, and/or another integrated system can include, but is not limited to, some or all of the following functionality, as described in further detail herein and in the Related Applications:

A. Estimating and/or displaying intravascular volume loss to hemodynamic decompensation (or cardiovascular collapse).

B. Estimating, predicting, and/or displaying a patient's compensatory reserve as an index that is proportional to an approximate measure of intravascular volume loss to CV collapse, recognizing that each patient has a unique reserve capacity.

C. Estimating, predicting, and/or displaying a patient's compensatory reserve as an index with a normative value at euvolemia (for example, CRI=1), representing a state in which the patient is normovolemic; a minimum value (for example, CRI=0) which implies no circulatory reserve and that the patient is experiencing CV collapse; and/or an excess value (for example, CRI>1) representing a state in which the patient is hypervolemic; the patient's normalized compensatory reserve can be displayed on a continuum between the minimum and maximum values (perhaps labeled by different symbols and/or colors depending on where the patient falls on the continuum).

D. Determining and/or displaying a probability that bleeding or intravascular volume loss has occurred.

E. Displaying an indicator that intravascular volume loss has occurred and/or is ongoing; as well as other measures of reserve, such as trend lines.

F. Estimating a patient's current blood pressure and/or predicting a patient's future blood pressure.

G. Estimating the current effectiveness of fluid resuscitation efforts.

H. Predicting the future effectiveness of fluid resuscitation efforts.

I. Estimating and/or predicting a volume of fluid necessary for effective resuscitation.

J. Estimating a probability that a patient needs fluids.

K. Estimating a hydration state of a patient or user.

L. Predicting a future hydration state of a patient or user.

M. Estimating and/or predicting a volume of fluid intake necessary for adequate hydration of a patient or user.

N. Estimating a probability that a patient is dehydrated.

In various embodiments, CRI, BL, V, and/or $P_f$ estimates can be (i) based on a fixed time history of patient monitoring (for example a 30 second or 30 heart beat window); (ii) based on a dynamic time history of patient monitoring (for example monitoring for 200 minutes, the system may use all sensor information gathered during that time to refine and improve CRI estimates, hydration effectiveness assessments, etc.); (iii) based on either establishing baseline estimates when the patient is normovolemic (no volume loss has occurred); and/or (iv) based on NO baselines estimates when patient is normovolemic.

Certain embodiments can also recommend treatment options, based on the analysis of the patient's condition (including the estimated/predicted blood pressure, probability of bleeding, state of dehydration, and/or the patient's estimated and/or predicted CRI). Treatment options can include, without limitation, such things as optimizing hemodynamics, ventilator adjustments, IV fluid adjustments (e.g., controlling the flow rate of an IV pump or the drip rate of an IV drip), transfusion of blood or blood products, infusion of volume expanders, medication changes, changes in patient position, and/or surgical therapy, or the like.

As one example, certain embodiments can be used to control an IV drip, IV pump, or rapid infuser. For instance, an embodiment might estimate the probability that a patient requires fluids and might activate such a device in response to that estimate (or instruct a clinician to attach such a device to the patient and activate the device). The system might then monitor the progress of the hydration effort (through continual or periodic assessment of the effectiveness of hydration) and increase/decrease drip or flow rates accordingly.

As another example, certain embodiments can be used as an input for a hemodialysis procedure. For example, certain embodiments can predict how much intravascular (blood) volume can be safely removed from a patient during a hemodialysis process. For example, an embodiment might provide instructions to a human operator of a hemodialysis machine, based on estimates or predictions of the patient's CRI. Additionally and/or alternatively, such embodiments can be used to continuously self-adjust the ultra-filtration rate of the hemodialysis equipment, thereby completely avoiding intradialytic hypotension and its associated morbidity.

As yet another example, certain embodiments can be used to estimate and/or predict a dehydration state (and/or the amount of dehydration) in an individual (e.g., a trauma patient, an athlete, an elder living at home, etc.) and/or to provide treatment (either by providing recommendations to treating personnel or by directly controlling appropriate therapeutic equipment). For instance, if an analytical model indicates a relationship between CRI (and/or any other physiological phenomena that can be measured and/or estimated using the techniques described herein and in the Related Applications) and dehydration state, an embodiment can apply that model, using the techniques described herein, to estimate a dehydration state of the patient.

Specific Exemplary Embodiments

We now turn to the embodiments as illustrated by the drawings. FIGS. 1-5 illustrate some of the features of the method, system, and apparatus for implementing physiological monitoring, and, more particularly, to methods, systems, and apparatuses for implementing device-based maneuver and activity state-based physiologic status monitoring, as referred to above. The methods, systems, and apparatuses illustrated by FIGS. 1-5 refer to examples of different embodiments that include various components and steps, which can be considered alternatives or which can be used in conjunction with one another in the various embodiments. The description of the illustrated methods, systems, and apparatuses shown in FIGS. 1-5 is provided for purposes of illustration and should not be considered to limit the scope of the different embodiments.

With reference to the figures, FIG. 1 is a schematic diagram illustrating a system 100 for implementing device-based maneuver and activity state-based physiologic status monitoring, in accordance with various embodiments.

In the non-limiting embodiment of FIG. 1, system 100 might comprise one or more sensor devices 105, which might include, without limitation, one or more sensors 110a-110n (collectively, "sensors 110" or the like). According to some embodiments, the one or more sensors 110 might include, without limitation, at least one of one or more accelerometers, one or more gyroscopes, one or more location sensors, one or more pedometers, one or more compasses, or one or more altimeters, and/or the like. Alternatively, or additionally, the one or more sensors 110 might include, but are not limited to, at least one of one or more skin temperature sensors; one or more moisture sensors; one or more resistance sensors; one or more electrodermal activity ("EDA") sensors; one or more body temperature sensors; one or more core temperature sensors; one or more fluid intake measurement sensors; one or more sensors measuring a compensatory reserve index ("CRI") of the user; one or more sensors measuring hemodynamic status of the user; one or more sensors measuring closeness of hemodynamic collapse due to at least one of heat stress, hydration, or central fluid loss; one or more sensors that continuously capture one or more pulsatile components of a cardiac cycle of the user; one or more electrocardiograph sensors; or one or more respiration rate sensors; and/or the like. In some instances, the one or more sensors that continuously capture the one or more pulsatile components of the cardiac cycle of the user might include, without limitation, at least one of radio frequency ("RF") sensor, a photoplethysmograph ("PPG"), a volume clamp, or a continuous blood pressure ("BP") sensor, and/or the like.

In some embodiments, the one or more sensors 110 may further include one or more positional sensors, which may include, without limitation, accelerometers, gyroscopes, global navigation satellite system (GNSS) receivers, or other positional sensors. In some embodiments, the user device 120 and/or computing system may be configured to mitigate motion artifacts from acquired pulsatile waveform data and/or other waveform data (e.g., PPG, BP, etc.) based, at least in part, on motion data acquired from the one or more positional sensors. Motion artifacts, for example, may include noise introduced to the pulsatile waveform data collected by the one or more sensors 110.

In some cases, the one or more sensors 110 might be embodied outside of (or external to) the one or more sensor devices 105 (not shown). Alternatively, the one or more sensors 110 might each be encapsulated within a sensor device (e.g., sensor device 105 (as shown in FIG. 1), where each sensor device 105 might include, but is not limited to, one of a patch-based sensor device, a wrist strap-based sensor device, an arm strap-based sensor device, a head band-based sensor device, a belt-based sensor device, a leg strap-based sensor device, an ankle strap-based sensor device, or a shoe strap-based sensor device, and/or the like. In yet another alternative embodiment, a combination (not shown) of external sensors 110 (i.e., embodied external to sensor devices 105) and encapsulated sensors 110 (i.e., embedded within sensor devices 105) might be implemented. According to some embodiments, the sensor(s) 110 and/or the sensor device(s) 105 may be removably attached or affixed to a user 115. In some cases, the sensor(s) 110 and/or the sensor device(s) 105 may be removably attached or affixed to the user 115 via at least one of a patch, a wrist strap, an arm strap, a head band, a belt, a leg strap, an ankle strap, or a shoe strap, and/or the like.

In some embodiments, system 100 might further comprise one or more user devices 120 and one or more environmental sensors 125a-125n (collectively, "environmental sensors 125" or "sensors 125" or the like). In some cases, the user device(s) 120 might each include, without limitation, one of a smart phone, a mobile phone, a smart watch, a tablet computer, a laptop computer, a desktop computer, or a dedicated sensor control device, and/or the like. In some instances, the environmental sensor(s) 125 might comprise sensors that measure or monitor one or more ambient environmental conditions, including, but not limited to, at least one of moisture, humidity, rainfall, temperature, atmospheric pressure, air quality, windspeed, windchill, or altitude, and/or the like. Accordingly, environmental sensors 125 may include, without limitation, a thermometer, altimeter, barometer, particulate matter sensor, carbon dioxide detector, carbon monoxide detector, among other suitable sensors.

According to some embodiments, system 100 might further comprise a (remote) computing system 130 and corresponding database(s) 135 that communicatively couples to the user device(s) 120 and/or at least one of sensor device(s) 105, sensor(s) 110, and/or sensor(s) 125, via network(s) 140. In some cases, system 100 might further comprise CRI server(s) 145 and corresponding database(s) 150 that may communicatively couple to at least one of the computing system 130, the user device(s) 120, the sensor device(s) 105, the sensor(s) 110, and/or the sensor(s) 125, via network(s) 140. According to various embodiments, the user device(s) 120 might communicatively couple to each of at least one of network(s) 140, sensor device(s) 105, sensor(s) 110, and/or sensor(s) 125, via wireless communications systems or technologies (including, but not limited to, Bluetooth™ communications, Z-wave communications, ZigBee communications, XBee communications, or WiFi communications, and/or the like), as denoted in FIG. 1 by the lightning bolt symbols. In some cases, the network(s) 140 might include a local area network ("LAN"), including, without limitation, a fiber network, an Ethernet network, a Token-Ring™ network, and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 802.11 suite of protocols, the Bluetooth™ protocol known in the art, the Z-Wave protocol known in the art, the ZigBee protocol or other IEEE 802.15.4 suite of protocols known in the art, and/or any other wireless protocol; and/or any combination of these and/or other networks. In a particular embodiment, the network might include an access network of the service provider (e.g., an Internet service provider ("ISP")). In another embodiment, the network might include a core network of the service provider, and/or the Internet.

In operation, the one or more sensors 110 and/or the sensor device(s) 105 (collectively, "one or more first sensors" or the like) might monitor at least one of one or more postures or one or more motions, and/or the like of the user 115, and might send data regarding the monitored at least one of the one or more postures or the one or more motions of the user, and/or the like (which might constitute physiological data of the user 115) to user device(s) 120 and/or computing system 130 (collectively, "computing system" or the like). In some cases, monitoring, with the one or more first sensors, the at least one of the one or more postures or the one or more motions of the user, and/or the like might comprise measuring relative positions of two or more of a head of the user, a neck of the user, a shoulder of the user, a chest of the user, a shoulder of the user, an upper arm of the user, an elbow of the user, a wrist of the user, a hand of the user, a finger of the user, a stomach of the user, a hip of the user, a leg of the user, a knee of the user, a calf of the user, an ankle of the user, a foot of the user, or a toe of the user, and/or the like. In some instances, sending the data regarding the monitored at least one of the one or more postures or the one or more motions of the user, and/or the like might comprise sending, with the one or more first sensors and to the computing system, data regarding the monitored at least one of the one or more postures or the one or more motions of the user, and/or the like, via wireless communications (as described above).

Alternatively, or additionally, user 115 might utilize a user interface (not shown) of the user device 120 (which may be associated with the user 115) to issue or otherwise speak a verbal command to initiate sensor recording as the user is in one of a body state or a transition between two body states among the at least one of the one or more body states or the one or more transitions between body states of the user, and/or the like. The user device 120 might then send the received verbal command to the one or more first sensors to initiate sensor recording. In response to receiving the verbal command to initiate sensor recording, the one or more first sensors might initiate sensor recording to monitor at least one of one or more postures or one or more motions of the user, and/or the like. The computing system might subsequently or concurrently store in a datastore (e.g., database 135 or the like) an association between the initiated sensor recording and the one of the body state or the transition between the two body states, and/or the like, corresponding to the received verbal command. The one or more first sensors might subsequently send to the computing system data regarding the monitored at least one of the one or more postures or the one or more motions of the user, and/or the like, where the physiological data of the user might include, but is not limited to, the data regarding the monitored at least one of the one or more postures or the one or more motions of the user and data regarding the association between the initiated sensor recording and the one of the body state or the transition between the two body states, and/or the like, corresponding to the received verbal command.

In some embodiments, the user device 120 may further be configured to store one or more recordings of verbal commands issued by the user 115. For example, in some embodiments, the user device 120 may be configured to store a log of verbal commands that includes one or more audio recordings of the issued verbal commands. The user device 120 may include, for example, a microphone configured to capture the user's 115 verbal command. In some embodiments, the user device 120 may be configured to determine, based on the one or more recordings of verbal commands, a physiological state of the user 115. For example, in some embodiments, the user device 120 may be configured to identify, based on one or more of the recordings, whether the user 115 is slurring, confused, stuttering, repeating, or exhibiting other speech-based symptoms indicative of a decline in the mental cognition of the user 115.

Alternatively, or additionally, the one or more first sensors might monitor the physiological state of the user 115, including, but not limited to, at least one of skin temperature, moisture, resistance, conductivity, sodium, salt, or other electrolyte content of perspiration on the skin, electrodermal activity ("EDA"), body temperature, core temperature, fluid intake amount, CRI, hemodynamic status, closeness of hemodynamic collapse due to at least one of heat stress, hydration, and/or central fluid loss, one or more pulsatile components of a cardiac cycle, electrical activity of the heart, respiration rate, blood pressure, and/or the like. Concurrently, the one or more environmental sensors 125 might monitor one or more ambient environmental conditions (near or around the user; particularly, as the physiological state of the user is being monitored), the one or more ambient environmental conditions including, without limitation, one of moisture, humidity, rainfall, temperature, atmospheric pressure, air quality, windspeed, windchill, or altitude, and/or the like.

In some aspects, the computing system (which might include the user device(s) 120 and/or the computing system 130, or the like) might receive physiological data of the user—which might include, without limitation, the data sent by the one or more first sensors, as described above; the data regarding the association between the initiated sensor recording and the one of the body state or the transition between the two body states, and/or the like, corresponding to the received verbal command, as described above; or the data regarding the ambient environmental conditions sent by the sensors 125, as described above; and/or the like. The computing system might analyze the received physiological data of the user to identify at least one of one or more body states or one or more transitions between body states of the user—that is, one of a face-up prone state of the user, a face-down prone state of the user, a sitting state of the user, a standing state of the user, a planking state of the user, a squatting state of the user, a walking state of the user, a running state of the user, a jumping state of the user, or an exercise state of the user, and/or the like, or one or more transitions between two of these body states. The computing system might determine at least one physiological state of the user, based at least in part on an analysis of the identified at least one of the one or more body states or the one or more transitions between body states of the user (or based at least in part on one or more of the analysis of the identified at least one of the one or more body states or the one or more transitions between body states of the user, an analysis of the monitored physiological state of the user, or an analysis of the monitored one or more ambient environmental conditions, and/or the like).

In some further embodiments, the computing system may further determine a physiological state of the used based on the physiological data of the user 115 in combination with one or more recordings of verbal commands issued by the user 115. For example, in some embodiments, physiological data may include sodium content of the user's 115 skin, as determined based on data generated by the one or more first sensors above. The sodium content of the user's skin may further be associated with the earlier described determination of slurring, stuttering, or other irregular speech patterns indicative of cognitive impairment or decline in the user 115. Based on a combination of the sodium content and recorded verbal commands, the computing system may be configured to determine a physiological state such as hyponatremia or hypernatremia. For example, electrolyte (e.g., sodium) imbalance in the body may induce hypo- or hypernatremia, which may cause temporary loss of mental cognition and confusion. Accordingly, a combination of contact sensor data and recorded verbal commands may be utilized, by the computing system, to determine whether the user 115 is experiencing hypo- or hypernatremia. In yet further embodiments, one or more positional sensors may further provide motion data, which may be combined with contact sensor data indicative of salt content on the skin, in perspiration (e.g., sweat), or saliva, and recorded verbal commands to determine whether the user 115 is experiencing hypo- or hypernatremia.

In some embodiments, the user device 120 may be configured to analyze the recorded voice recording, or to provide the voice recording to the computing system for analysis. In some embodiments, the user device 120 and/or computing system may employ an artificial intelligence (AI)/machine learning (ML) algorithm configured to detect irregular speech patterns based on the one or more recordings of verbal commands. Thus, in some embodiments, the user device 120 and/or computing system may be configured to automatically detect irregular speech patterns. In other embodiments, the user device 120 and/or computing system may be configured to provide the recorded verbal commands to a medical provider for diagnosis by the medical provider (e.g., a clinician, treating physician, etc.).

In some further embodiments, the computing system may be configured to determine a physiological state of the user 115 based on one or more environmental sensors 125 described above. For example, in some embodiments, the environmental sensor(s) 125 may indicate an ambient temperature which may be associated with the occurrence of hypo- or hyperthermia. Environmental data may then be combined with physiological data to determine a physiological state of the user 115. In one example, an ambient temperatures measuring 10 degrees Celsius or cooler combined with body temperatures of 35 degrees Celsius or cooler may indicate that a user is experiencing hypothermia. Conversely, ambient temperatures of 27 degrees Celsius or higher and a body temperature of 40 degrees Celsius or higher may be used by the computing system to determine that the user 115 is experiencing hyperthermia. In other example, other combinations of physiological data and environmental data may be used to determine other physiological states. For example, pulse oximeter/oxygen saturation (SpO2) and carbon dioxide ($CO_2$) levels may be used to determine whether the user 115 is experiencing hypoxemia. Respiration rate and particulate matter measurements (e.g., air pollution) may be used to determine whether the patient is experiencing respiratory irritation or dysfunction.

Merely by way of example, in some cases, the at least one physiological state of the user might include, without limitation, at least one of a hydration state of the user, a dehydration state of the user, a fitness state of the user, a health state of the user, an exertion readiness state of the user, a fatigue state of the user, an alertness level of the user, an altitude sickness state of the user, a level of tolerance to heat of the user, a level of tolerance to cold of the user, a level of tolerance to other environmental conditions of the user, a level of tolerance to liquid limitations of the user, a level of tolerance to blood loss of the user, or one or more states of illness of the user (including, but not limited to, flu, cold, viral infection, bacterial infection, sepsis, heart disease, and/or the like), and/or the like.

The computing system might then send the determined at least one physiological state of the user to the user device(s) 120 of the user for display on a display screen of the user device(s) 120.

According to some embodiments, implementation of software and algorithms (which may be performed on the user device(s) 120, the computing system 130, or other computational device(s)) may include, without limitation, (A) methodology for mapping one or more recorded timelines of motion tracking sensor readings to associated body states and transitions between body states—the algorithmic method for performing such mapping including, but not limited to, deep learning, clustering unsupervised and semi-supervised algorithms, principle component analysis and related linear and non-linear techniques such as independent component analysis and network component analysis, Mahalanobis distance and Polynomial Mahalanobis Distance Metric, minimum (or percent of) and maximum (or percent of) sensor readings during relevant time intervals, supervised learning techniques, or probabilistic methods yielding estimates of confidence, and/or the like; (B) methodology for mapping the results of characterized recording timelines in (A) above to status and/or prediction of future status—the algorithmic method for performing such mapping including, but not limited to, deep learning, supervised learning techniques, or probabilistic methods yielding estimates of confidence, and/or the like; or (C) methodology for mapping the results of characterized recording timelines in (B) above to status and/or prediction of future status—the algorithmic method for performing such mapping including, but not limited to, deep learning, supervised learning techniques, or probabilistic methods yielding estimates of confidence, and/or the like.

Alternatively, implementation of software and algorithms (which may be performed on the user device(s) 120, the computing system 130, or other computational device(s)) may include, without limitation, (D) methodology for mapping one or more recorded timelines of sensor readings to associated body states and transitions between body states—the algorithmic method for performing such mapping including, but not limited to, deep learning, clustering unsupervised and semi-supervised algorithms, principle component analysis and related linear and non-linear techniques such as independent component analysis and network component analysis, Mahalanobis distance and Polynomial Mahalanobis Distance Metric, or minimum (or percent of) and maximum (or percent of) sensor readings during relevant time intervals, and/or the like; or (E) methodology for mapping the results of characterized recording timelines in (D) above to status and/or prediction of future status—the algorithmic method for performing such mapping including, but not limited to, deep learning, supervised learning techniques, or probabilistic methods yielding estimates of confidence, and/or the like.

According to some aspects, a measurement of compensatory reserve, as characterized by a compensatory reserve index (which is described in detail in the Related Applications, which have already been incorporated herein by reference in their entirety for all purposes), may be indicative of a body state of the user 115. In particular, the inventors of this application have found that physical activity or a change in physical activity of the user 115 (e.g., a body state (as described above) or a transition between body states (as also described above)) may result in an impulse response in the CRI of the user. Profiles of the CRI (as compared with base measurements of CRI of the individual user or a compilation of measurements of CRI across a sample of multiple users) may be indicative of health, fitness, and/or other physiological states of the user. In such cases, a CRI server (e.g., CRI server(s) 145 or the like) or other computational device might monitor physiological data of the user 115 (e.g., by using sensors, including, but not limited to the one or more first sensors, as described above) to measure a CRI of the user 115, and might further analyze the measured CRI to determine a body state of the user 115 and/or a transition between body states of the user 115, and might also further analyze the measured CRI to determine the physiological state of the user—including, but not limited to, at least one of a hydration state of the user, a dehydration state of the user, a fitness state of the user, a health state of the user, an exertion readiness state of the user, a fatigue state of the user, an alertness level of the user, an altitude sickness state of the user, a level of tolerance to heat of the user, a level of tolerance to cold of the user, a level of tolerance to other environmental conditions of the user, a level of tolerance to liquid limitations of the user, a level of tolerance to blood loss of the user, or one or more states of illness of the user (including, but not limited to, flu, cold, viral infection, bacterial infection, sepsis, heart disease, and/or the like), and/or the like. Such physiological states may then be presented to the user 115 (or a physician or other healthcare provider of the user 115) using a user interface of a user device (e.g., user device(s) 120, or the like), a display screen of a user device (e.g., user device(s) 120, or the like), a web portal, a software application ("app"), and/or the like.

In some embodiments, the physiological state determination may be performed in real-time or near-real-time based on the monitored sensor data (i.e., physiological data collected or monitored by the one or more first sensors).

These and other functions of the system 100 (and its components) are described in greater detail below with respect to FIGS. 2-4.

Figure 2:
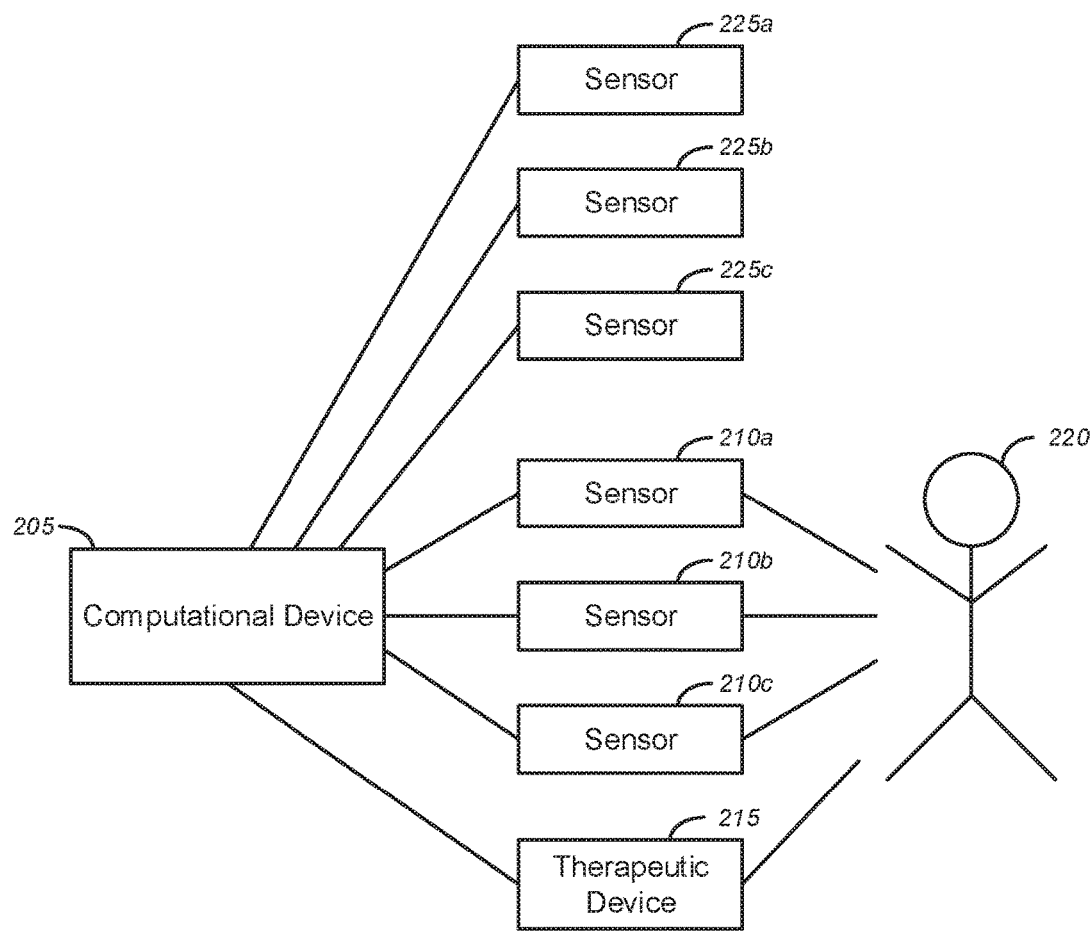
FIG. 2 is a schematic diagram illustrating a system for estimating compensatory reserve, which can be used for implementing device-based maneuver and activity state-based physiologic status monitoring, in accordance with various embodiments.

FIG. 2 is a schematic diagram illustrating a system 200 for estimating compensatory reserve, which can be used for implementing device-based maneuver and activity state-based physiologic status monitoring, in accordance with various embodiments.

FIG. 2 provides a general overview of a system 200 provided by certain embodiments. The system might include a computer system or computational device 205 in communication with one or more sensors 210 (which might include sensors 210a, 210b, and 210c, or the like), each of which might be configured to obtain physiological data from the subject (e.g., animal or human test subject or patient) 220. In one embodiment, the computer system 205 might comprise a Lenovo THINKPAD X200, 4 GB of RAM with Microsoft WINDOWS 7 operating system and might be programmed with software to execute the computational methods outlined herein or in the Related Applications. The computational methods can be implemented in MATLAB 2009b and C++ programming languages. A more general example of a computer system 205 that can be used in some embodiments is described in further detail below. Even more generally, however, the computer system 205 can be any system of one or more computers that are capable of performing the techniques described herein. In a particular embodiment, for example, the computer system 205 is capable of reading values from the physiological sensors 210; generating models of physiological state from those sensors; employing such models to make individual-specific estimations, predictions, or other diagnoses; displaying the results; recommending and/or implementing a therapeutic treatment as a result of the analysis; and/or archiving (learning) these results for use in future, model building and predictions; or the like.

The sensors 210 can be any of a variety of sensors (including, without limitation, those described herein) for obtaining physiological data from the subject. An exemplary sensor suite might include a Finometer sensor for obtaining a noninvasive continuous blood pressure waveform, a pulse oximeter sensor, an Analog to Digital Board (National Instruments USB-9215A 16-Bit, 4 channel) for connecting the sensors (either the pulse oximeter and/or the finometer) to the computer system 205. More generally, in an embodiment, one or more sensors 210 might obtain, e.g., using one or more of the techniques described herein, continuous physiological waveform data, such as continuous blood pressure. Input from the sensors 210 can constitute continuous data signals and/or outcomes that can be used to generate, and/or can be applied to, a predictive model as described below.

Merely by way of example, the one or more sensors 210 might include, without limitation, at least one of one or more accelerometers, one or more gyroscopes, one or more location sensors, one or more pedometers, one or more compasses, or one or more altimeters, and/or the like. Alternatively, or additionally, the one or more sensors 210 might include, but are not limited to, at least one of one or more skin temperature sensors; one or more moisture sensors; one or more resistance sensors; one or more electrodermal activity ("EDA") sensors; one or more body temperature sensors; one or more core temperature sensors; one or more fluid intake measurement sensors; one or more sensors measuring a compensatory reserve index ("CRI") of the user; one or more sensors measuring hemodynamic status of the user; one or more sensors measuring closeness of hemodynamic collapse due to at least one of heat stress, hydration, or central fluid loss; one or more sensors that continuously capture one or more pulsatile components of a cardiac cycle of the user; one or more electrocardiograph sensors; or one or more respiration rate sensors; and/or the like. In some instances, the one or more sensors that continuously capture the one or more pulsatile components of the cardiac cycle of the user might include, without limitation, at least one of radio frequency ("RF") sensor, a photoplethysmograph ("PPG"), a volume clamp, or a continuous blood pressure ("BP") sensor, and/or the like.

In some cases, the structure or system might include a therapeutic device 215 (also referred to herein as a "physiological assistive device"), which can be controlled by the computer system 205 to administer therapeutic treatment, in accordance with the recommendations developed by analysis of a patient's physiological data. In a particular embodiment, the therapeutic device might comprise hemodialysis equipment (also referred to as a hemodialysis machine), which can be controlled by the computer system 205 based on the estimated CRI of the patient, as described in further detail below. Further examples of therapeutic devices in other embodiments can include a cardiac assist device, a ventilator, an automatic implantable cardioverter defibrillator ("AICD"), pacemakers, an extracorporeal membrane oxygenation circuit, a positive airway pressure ("PAP") device (including, without limitation, a continuous positive airway pressure ("cPAP") device, or the like), an anesthesia machine, an integrated critical care system, a medical robot, intravenous and/or intra-arterial pumps that can provide fluids and/or therapeutic compounds (e.g., through intravenous injection), intravenous drips, a rapid infuser, a heating/cooling blanket, and/or the like.

According to some embodiments, system 200 might further comprise one or more environmental sensors 225 (which might include sensors 225a, 225b, and 225c, or the like), which may be used might monitor one or more ambient environmental conditions (near or around the user; particularly, as the physiological state of the user is being monitored), the one or more ambient environmental conditions including, without limitation, one of moisture, humidity, rainfall, temperature, atmospheric pressure, air quality, windspeed, windchill, or altitude, and/or the like.

System 200 of FIG. 2 might otherwise be implemented in a similar manner as described in detail herein with respect to system 100 of FIG. 1 or method 400 of FIG. 4.

Figure 3:
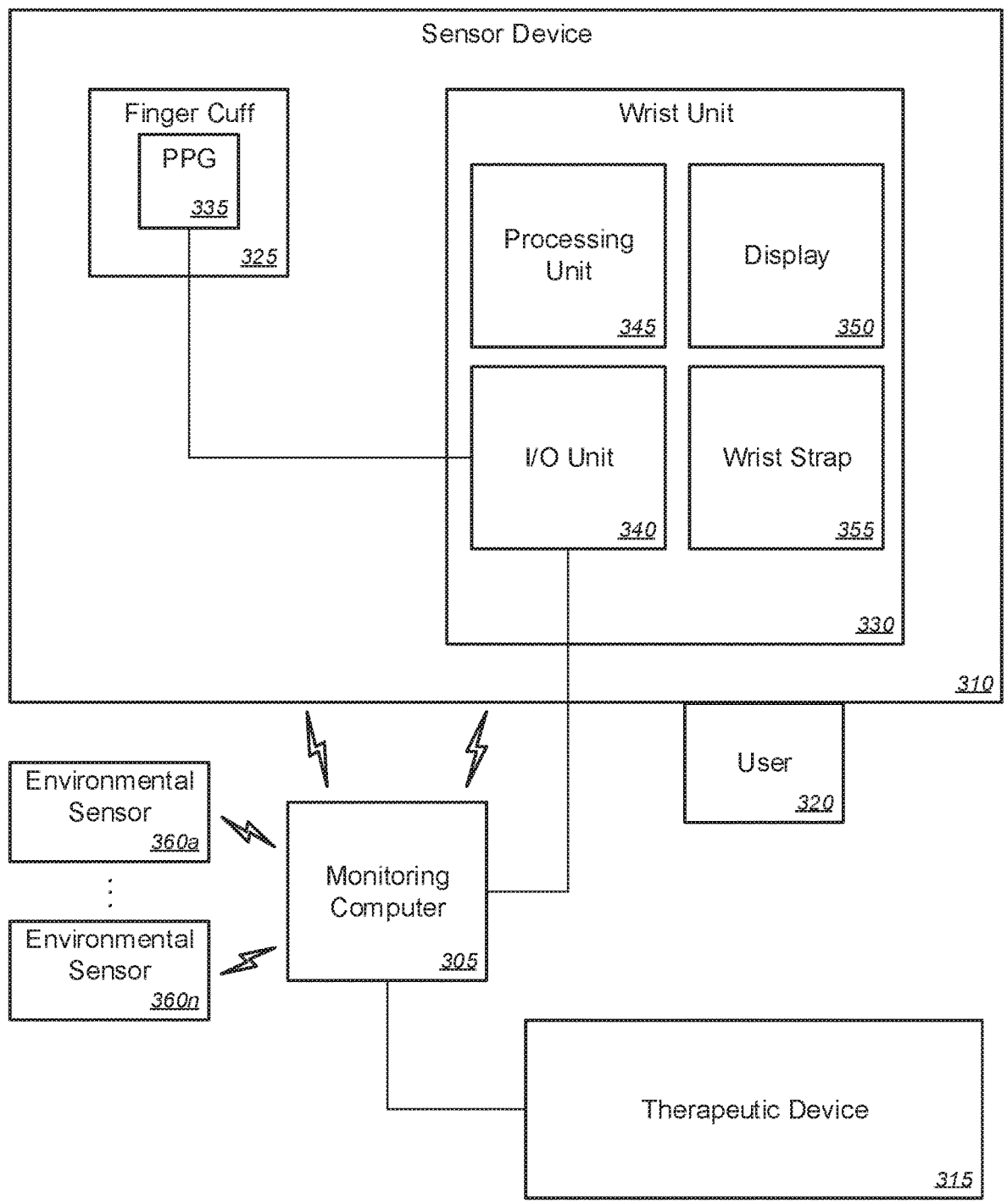
FIG. 3 is a schematic diagram illustrating an example of a sensor system that can be worn on a patient's body and that can be used for implementing device-based maneuver and activity state-based physiologic status monitoring, in accordance with various embodiments.

FIG. 3 is a schematic diagram illustrating an example 300 of a sensor system that can be worn on a patient's body and that can be used for implementing device-based maneuver and activity state-based physiologic status monitoring, in accordance with various embodiments.

FIG. 3 illustrates in more detail an exemplary sensor device 310, which can be used in the system 300. (It should be noted, of course, that the depicted sensor device 310 of FIG. 3 is not intended to be limiting, and different embodiments can employ any sensor that captures suitable data, including, without limitation, sensors described elsewhere in this disclosure and in the Related Applications.) The illustrated sensor device 310 is designed to be worn on a patient (e.g., user 320) such as (but not limited to) on the patient's wrist and therefore can be used both in clinical settings and in the field (e.g., on any person for whom monitoring might be beneficial, for a variety of reasons, including, without limitation, assessment of blood pressure and/or hydration during athletic competition or training, daily activities, military training or action, etc.). In one aspect, the sensor device 310 can serve as an integrated hydration monitor, which can assess hydration as described in some of the Related Applications, display an indication of the assessment, recommend therapeutic action based on the assessment, or the like, in a form factor that can be worn during athletic events and/or daily activities. Alternatively, or additionally, the sensor device 310 can serve to monitor maneuvers (or motions) of the patient as well as activities of the patient to identify or determine a body state or transition between body states of the patient, and subsequently to determine a physiological state of the patient based at least in part on the determined body state or transition between body states of the patient (and perhaps also based at least in part on data, e.g., CRI data, of the patient and/or of a plurality of other patients or users). In other words, the system might be able to determine physiological states of the patient, including, but not limited to, at least one of a hydration state of the user, a dehydration state of the user, a fitness state of the user, a health state of the user, an exertion readiness state of the user, a fatigue state of the user, an alertness level of the user, an altitude sickness state of the user, a level of tolerance to heat of the user, a level of tolerance to cold of the user, a level of tolerance to other environmental conditions of the user, a level of tolerance to liquid limitations of the user, a level of tolerance to blood loss of the user, or one or more states of illness of the user (including, but not limited to, flu, cold, viral infection, bacterial infection, sepsis, heart disease, and/or the like), and/or the like.

Hence, the exemplary sensor 310 device (e.g., physiological monitor or the like) might include a finger cuff 325 and a wrist unit 330. The finger cuff 325 might, in some cases, include a fingertip sensor 335 (in this case, a PPG sensor, or the like) that captures data based on physiological conditions of the patient, such as PPG waveform data, or the like. The sensor 335 communicates with an input/output unit 340 of the wrist unit 330 to provide output from the sensor 335 to a processing unit 345 of the wrist unit 330. Such communication can be wired (e.g., via a standard—such as USB—or proprietary connector on the wrist unit 330) and/or wireless (e.g., via Bluetooth, such as Bluetooth Low Energy ("BTLE"), near field connection ("NFC"), WiFi, ZigBee, XBee, Z-Wave, or any other suitable radio technology).

In different embodiments, the processing unit 345 can have different types of functionality. For example, in some cases, the processing unit 345 might simply act to store and/or organize data prior to transmitting the data through the I/O unit 340 to a monitoring computer 305, which might perform data analysis, to control a therapeutic device 315 (as described in some of the Related Applications, or the like), etc. In other cases, however, the processing unit 345 might act as a specialized computer (e.g., with some or all of the components described in connection with FIG. 1 above, and/or some or all of the functionality ascribed to the computer 205 of FIG. 2, or the like), such that the processing unit 345 can perform data analysis onboard, e.g., to estimate and/or predict a patient's current and/or future physiological state. As such, the wrist unit 330 might include a display 350, which can display any output described herein, including, without limitation, estimated and/or predicted values (e.g., of CRI, blood pressure, hydration status, or physiological state in general, etc.), data captured by the sensor (e.g., heart rate, pulse oximetry data, etc.), and/or the like.

In some cases, the wrist unit 330 might include a wrist strap 355 that allows the unit to be worn on the wrist, similar to a wrist watch. Of course, other options are available to facilitate transportation of the sensor device 310 with a patient. More generally, the sensor device 310 might not include all of the components described above, and/or various components might be combined and/or reorganized.

According to some embodiments, system 300 might further comprise one or more environmental sensors 360a-360n (collectively, "environmental sensors 360" or "sensors 360" or the like), which may be used might monitor one or more ambient environmental conditions (near or around the user; particularly, as the physiological state of the user is being monitored), the one or more ambient environmental conditions including, without limitation, one of moisture, humidity, rainfall, temperature, atmospheric pressure, air quality, windspeed, windchill, or altitude, and/or the like. The ambient environmental conditions may be used to supplement or complement the physiological state data that is measured or monitored by sensor device 310.

Once again, the embodiment illustrated by FIG. 3 should be considered only illustrative, and not limiting, in nature. For example, although a wrist unit and a finger cuff are shown in FIG. 3, the various embodiments are not so limited, and the sensor device 310 may alternatively be embodied as a sensor device that may be removably attached or affixed to the user 320 via at least one of a patch, an arm strap, a head band, a belt, a leg strap, an ankle strap, or a shoe strap, and/or the like.

System 300 of FIG. 3 might otherwise be implemented in a similar manner as described in detail herein with respect to system 100 of FIG. 1 or method 400 of FIG. 4.

FIGS. 4A-4E (collectively, "FIG. 4") are flow diagrams illustrating a method for implementing device-based maneuver and activity state-based physiologic status monitoring, in accordance with various embodiments. Method 400 of FIG. 4B returns to FIG. 4A following the circular marker denoted, "A," while method 400 of FIG. 4C returns to FIG. 4A following the circular marker denoted, "B," and method 400 of FIG. 4D returns to FIG. 4A following the circular marker denoted, "C."

While the techniques and procedures are depicted and/or described in a certain order for purposes of illustration, it should be appreciated that certain procedures may be reordered and/or omitted within the scope of various embodiments. Moreover, while the method 400 illustrated by FIG. 4 can be implemented by or with (and, in some cases, are described below with respect to) the systems, examples, or embodiments 100, 200, and 300 of FIGS. 1, 2, and 3, respectively (or components thereof), such methods may also be implemented using any suitable hardware (or software) implementation. Similarly, while each of the systems, examples, or embodiments 100, 200, and 300 of FIGS. 1, 2, and 3, respectively (or components thereof), can operate according to the method 400 illustrated by FIG. 4 (e.g., by executing instructions embodied on a computer readable medium), the systems, examples, or embodiments 100, 200, and 300 of FIGS. 1, 2, and 3 can each also operate according to other modes of operation and/or perform other suitable procedures.

Figure 4A:
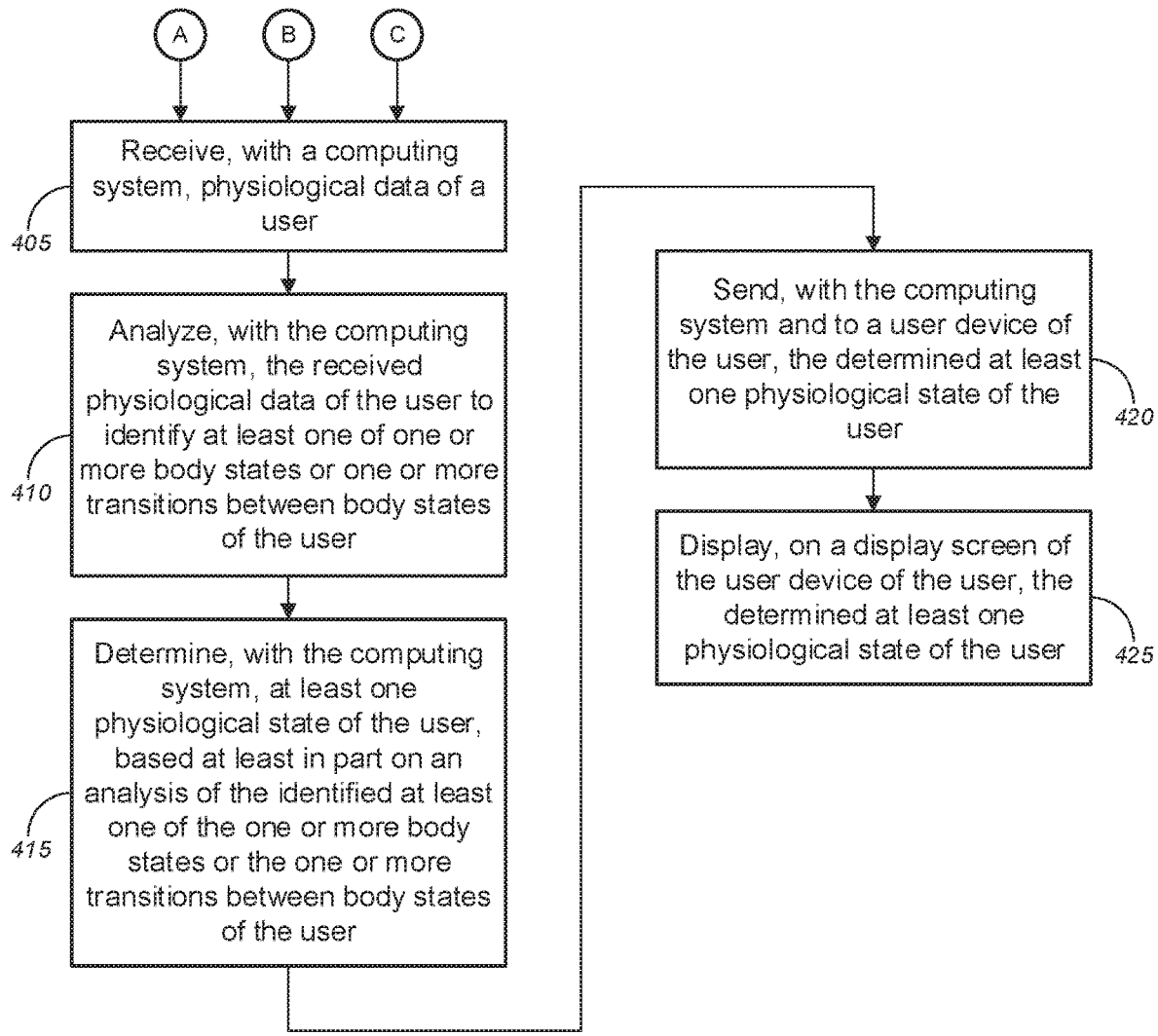

In the non-limiting embodiment of FIG. 4A, method 400, at block 405, might comprise receiving, with a computing system, physiological data of a user. At block 410, method 400 might comprise analyzing, with the computing system, the received physiological data of the user to identify at least one of one or more body states or one or more transitions between body states of the user. Method 400 might further comprise, at block 415, determining, with the computing system, at least one physiological state of the user, based at least in part on an analysis of the identified at least one of the one or more body states or the one or more transitions between body states of the user. Method 400 might further comprise sending, with the computing system and to a user device (e.g., a user device of the user, a user device of a physician or other healthcare provider of the user, etc.), the determined at least one physiological state of the user (block 420) and displaying, on a display screen of the user device, the determined at least one physiological state of the user (block 425).

In some embodiments, the one or more body states might each include, without limitation, one of a face-up prone state of the user, a face-down prone state of the user, a sitting state of the user, a standing state of the user, a planking state of the user, a squatting state of the user, a walking state of the user, a running state of the user, a jumping state of the user, or an exercise state of the user, and/or the like. In such cases, the one or more transitions between body states of the user might each include transitions between two of said one or more body states.

In some cases, the at least one physiological state of the user might include, without limitation, at least one of a hydration state of the user, a dehydration state of the user, a fitness state of the user, a health state of the user, an exertion readiness state of the user, a fatigue state of the user, an alertness level of the user, an altitude sickness state of the user, a level of tolerance to heat of the user, a level of tolerance to cold of the user, a level of tolerance to other environmental conditions of the user, a level of tolerance to liquid limitations of the user, a level of tolerance to blood loss of the user, or one or more states of illness of the user (including, but not limited to, flu, cold, viral infection, bacterial infection, sepsis, heart disease, and/or the like), and/or the like. According to some embodiments, the user device might include, but is not limited to, one of a smart phone, a mobile phone, a smart watch, a tablet computer, a laptop computer, a desktop computer, or a dedicated sensor control device, and/or the like.

With reference to the non-limiting embodiment of FIG. 4B, method 400 might further comprise monitoring, with one or more first sensors, at least one of one or more postures or one or more motions of the user, and/or the like (block 430); and sending, with the one or more first sensors and to the computing system, data regarding the monitored at least one of the one or more postures or the one or more motions of the user, and/or the like (block 435). In such cases, the physiological data of the user might comprise the data regarding the monitored at least one of the one or more postures or the one or more motions of the user, and/or the like.

In some embodiments, the one or more first sensors might include, without limitation, at least one of one or more accelerometers, one or more gyroscopes, one or more location sensors, one or more pedometers, one or more compasses, or one or more altimeters, and/or the like. Alternatively, or additionally, the one or more first sensors might each be encapsulated within a sensor device, where each sensor device might include, but is not limited to, one of a patch-based sensor device, a wrist strap-based sensor device, an arm strap-based sensor device, a head band-based sensor device, a belt-based sensor device, a leg strap-based sensor device, an ankle strap-based sensor device, or a shoe strap-based sensor device, and/or the like.

According to some embodiments, monitoring, with one or more first sensors, the at least one of the one or more postures or the one or more motions of the user, and/or the like (at block 430) might comprise measuring relative positions of two or more of a head of the user, a neck of the user, a shoulder of the user, a chest of the user, a shoulder of the user, an upper arm of the user, an elbow of the user, a wrist of the user, a hand of the user, a finger of the user, a stomach of the user, a hip of the user, a leg of the user, a knee of the user, a calf of the user, an ankle of the user, a foot of the user, or a toe of the user, and/or the like.

In some instances, sending the data regarding the monitored at least one of the one or more postures or the one or more motions of the user, and/or the like (at block 435) might comprise sending, with the one or more first sensors and to the computing system, data regarding the monitored at least one of the one or more postures or the one or more motions of the user, and/or the like, via wireless communications.

Method 400 might return to the process at block 405 in FIG. 4A following the circular marker denoted, "A," and method 400 might proceed as described above with respect to FIG. 4A using the data obtained by the one or more first sensors that monitor the postures and/or motions of the user.

Turning to the non-limiting embodiment of FIG. 4C, method 400 might further comprise, at block 440, receiving, with a user interface of the user device, a verbal command to initiate sensor recording as the user is in one of a body state or a transition between two body states among the at least one of the one or more body states or the one or more transitions between body states of the user, and/or the like. At block 445, method 400 might comprise sending, with the user device and to one or more first sensors, the received verbal command to initiate sensor recording. Method 400 might further comprise, in response to receiving the verbal command to initiate sensor recording, initiating, with the one or more first sensors, sensor recording to monitor at least one of one or more postures or one or more motions of the user, and/or the like (block 450) and storing, with the computing system and in a datastore, an association between the initiated sensor recording and the one of the body state or the transition between the two body states, and/or the like, corresponding to the received verbal command (block 455). Method 400, at block 460, might comprise sending, with the one or more first sensors and to the computing system, data regarding the monitored at least one of the one or more postures or the one or more motions of the user, and/or the like, where the physiological data of the user might include, but is not limited to, the data regarding the monitored at least one of the one or more postures or the one or more motions of the user and data regarding the association between the initiated sensor recording and the one of the body state or the transition between the two body states, and/or the like, corresponding to the received verbal command.

In some embodiments, similar to the embodiment of FIG. 4B, the one or more first sensors might include, without limitation, at least one of one or more accelerometers, one or more gyroscopes, one or more location sensors, one or more pedometers, one or more compasses, or one or more altimeters, and/or the like. Alternatively, or additionally, the one or more first sensors might each be encapsulated within a sensor device, where each sensor device might include, but is not limited to, one of a patch-based sensor device, a wrist strap-based sensor device, an arm strap-based sensor device, a head band-based sensor device, a belt-based sensor device, a leg strap-based sensor device, an ankle strap-based sensor device, or a shoe strap-based sensor device, and/or the like.

According to some embodiments, initiating, with the one or more first sensors, sensor recording to monitoring the at least one of the one or more postures or the one or more motions of the user, and/or the like (at block 450) might comprise measuring relative positions of two or more of a head of the user, a neck of the user, a shoulder of the user, a chest of the user, a shoulder of the user, an upper arm of the user, an elbow of the user, a wrist of the user, a hand of the user, a finger of the user, a stomach of the user, a hip of the user, a leg of the user, a knee of the user, a calf of the user, an ankle of the user, a foot of the user, or a toe of the user, and/or the like.

In some instances, sending the data regarding the monitored at least one of the one or more postures or the one or more motions of the user, and/or the like (at block 460) might comprise sending, with the one or more first sensors and to the computing system, data regarding the monitored at least one of the one or more postures or the one or more motions of the user, and/or the like, via wireless communications.

Method 400 might return to the process at block 405 in FIG. 4A following the circular marker denoted, "B," and method 400 might proceed as described above with respect to FIG. 4A using the data obtained by the one or more first sensors that monitor the postures and/or motions of the user and the data regarding the association between the initiated sensor recording and the one of the body state or the transition between the two body states, and/or the like, corresponding to the received verbal command.

Figures 4D, 4E:
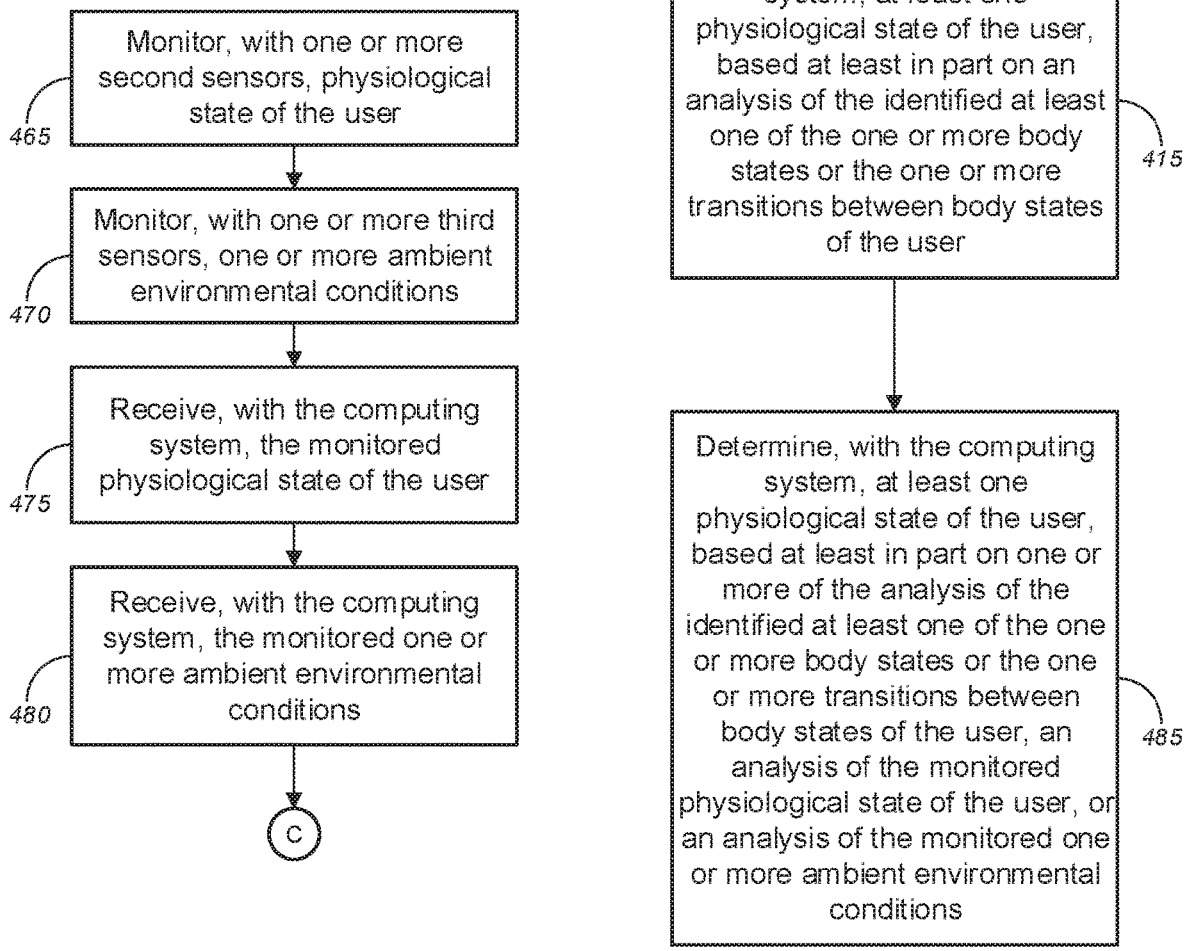

Referring to the non-limiting embodiment of FIG. 4D, method 400 might further comprise monitoring, with one or more second sensors, physiological state of the user (block 465); monitoring, with one or more third sensors, one or more ambient environmental conditions (near or around the user; particularly, as the physiological state of the user is being monitored) (block 470); receiving, with the computing system, the monitored physiological state of the user (block 475); and receiving, with the computing system, the monitored one or more ambient environmental conditions (block 480).

According to some embodiments, the one or more second sensors might each include, without limitation, one of one or more skin temperature sensors; one or more moisture sensors; one or more resistance sensors; one or more electrodermal activity ("EDA") sensors; one or more body temperature sensors; one or more core temperature sensors; one or more fluid intake measurement sensors; one or more sensors measuring a compensatory reserve index ("CRI") of the user; one or more sensors measuring hemodynamic status of the user; one or more sensors measuring closeness of hemodynamic collapse due to at least one of heat stress, hydration, or central fluid loss; one or more sensors that continuously capture one or more pulsatile components of a cardiac cycle of the user; one or more electrocardiograph sensors; or one or more respiration rate sensors; and/or the like. In some cases, the one or more sensors that continuously capture the one or more pulsatile components of the cardiac cycle of the user might include, but are not limited to, at least one of radio frequency ("RF") sensor, a photoplethysmograph ("PPG"), a volume clamp, or a continuous blood pressure ("BP") sensor, and/or the like.

In some embodiments, the one or more ambient environmental conditions might each include, without limitation, one of moisture, humidity, rainfall, temperature, atmospheric pressure, air quality, windspeed, windchill, or altitude, and/or the like.

Method 400 might return to the process at block 405 in FIG. 4A following the circular marker denoted, "C," and method 400 might proceed as described above with respect to FIG. 4A using data obtained by the one or more second sensors that monitor the physiological state of the user and/or data obtained by the one or more third sensors that monitor the one or more ambient environmental conditions (near or around the user; particularly, as the physiological state of the user is being monitored).

Merely by way of example, in some cases (and with reference to the non-limiting embodiment of FIG. 4E), determining, with the computing system, the at least one physiological state of the user (at block 415) might comprise determining, with the computing system, at least one physiological state of the user, based at least in part on one or more of the analysis of the identified at least one of the one or more body states or the one or more transitions between body states of the user, an analysis of the monitored physiological state of the user, or an analysis of the monitored one or more ambient environmental conditions, and/or the like (block 485).

Exemplary System and Hardware Implementation

Figure 5:
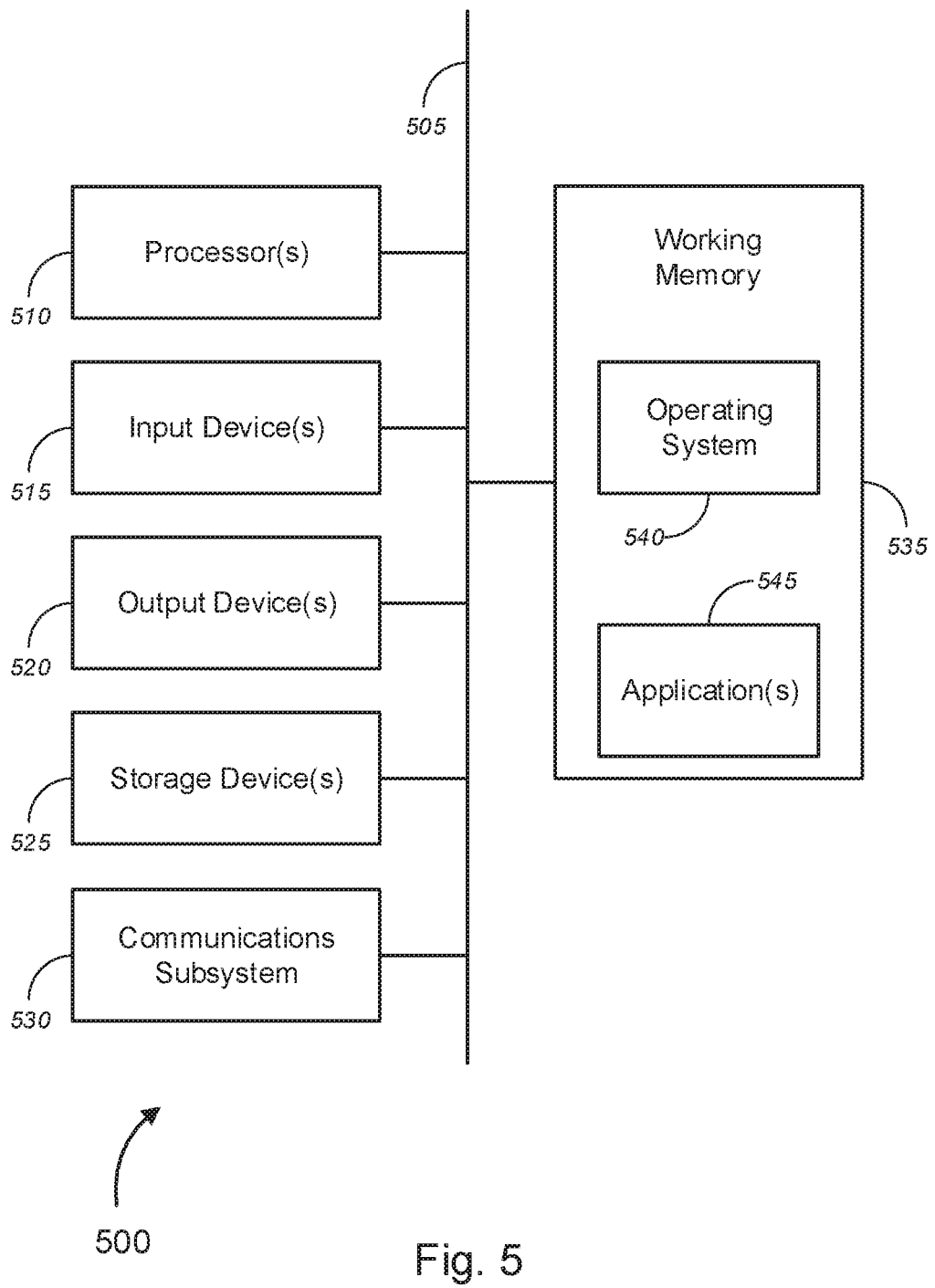
FIG. 5 is a block diagram illustrating an exemplary computer or system hardware architecture, in accordance with various embodiments.

FIG. 5 is a block diagram illustrating an exemplary computer or system hardware architecture, in accordance with various embodiments. FIG. 5 provides a schematic illustration of one embodiment of a computer system 500 of the service provider system hardware that can perform the methods provided by various other embodiments, as described herein, and/or can perform the functions of computer or hardware system (i.e., sensor devices 105 and 310, user devices 120, computing system 130, computational device 205, monitoring computer 305, compensatory reserve index ("CRI") server(s) 145, and therapeutic devices 215 and 315, etc.), as described above. It should be noted that FIG. 5 is meant only to provide a generalized illustration of various components, of which one or more (or none) of each may be utilized as appropriate. FIG. 5, therefore, broadly illustrates how individual system elements may be implemented in a relatively separated or relatively more integrated manner.

The computer or hardware system 500—which might represent an embodiment of the computer or hardware system (i.e., sensor devices 105 and 310, user devices 120, computing system 130, computational device 205, monitoring computer 305, CRI server(s) 145, and therapeutic devices 215 and 315, etc.), described above with respect to FIGS. 1-4—is shown comprising hardware elements that can be electrically coupled via a bus 505 (or may otherwise be in communication, as appropriate). The hardware elements may include one or more processors 510, including, without limitation, one or more general-purpose processors and/or one or more special-purpose processors (such as microprocessors, digital signal processing chips, graphics acceleration processors, and/or the like); one or more input devices 515, which can include, without limitation, a mouse, a keyboard, and/or the like; and one or more output devices 520, which can include, without limitation, a display device, a printer, and/or the like.

The computer or hardware system 500 may further include (and/or be in communication with) one or more storage devices 525, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable, and/or the like. Such storage devices may be configured to implement any appropriate data stores, including, without limitation, various file systems, database structures, and/or the like.

The computer or hardware system 500 might also include a communications subsystem 530, which can include, without limitation, a modem, a network card (wireless or wired), an infra-red communication device, a wireless communication device and/or chipset (such as a Bluetooth™ device, an 802.11 device, a WiFi device, a WiMax device, a WWAN device, cellular communication facilities, etc.), and/or the like. The communications subsystem 530 may permit data to be exchanged with a network (such as the network described below, to name one example), with other computer or hardware systems, and/or with any other devices described herein. In many embodiments, the computer or hardware system 500 will further comprise a working memory 535, which can include a RAM or ROM device, as described above.

The computer or hardware system 500 also may comprise software elements, shown as being currently located within the working memory 535, including an operating system 540, device drivers, executable libraries, and/or other code, such as one or more application programs 545, which may comprise computer programs provided by various embodiments (including, without limitation, hypervisors, VMs, and the like), and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 525 described above. In some cases, the storage medium might be incorporated within a computer system, such as the system 500. In other embodiments, the storage medium might be separate from a computer system (i.e., a removable medium, such as a compact disc, etc.), and/or provided in an installation package, such that the storage medium can be used to program, configure, and/or adapt a general purpose computer with the instructions/code stored thereon. These instructions might take the form of executable code, which is executable by the computer or hardware system 500 and/or might take the form of source and/or installable code, which, upon compilation and/or installation on the computer or hardware system 500 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware (such as programmable logic controllers, field-programmable gate arrays, application-specific integrated circuits, and/or the like) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer or hardware system (such as the computer or hardware system 500) to perform methods in accordance with various embodiments of the invention. According to a set of embodiments, some or all of the procedures of such methods are performed by the computer or hardware system 500 in response to processor 510 executing one or more sequences of one or more instructions (which might be incorporated into the operating system 540 and/or other code, such as an application program 545) contained in the working memory 535. Such instructions may be read into the working memory 535 from another computer readable medium, such as one or more of the storage device(s) 525. Merely by way of example, execution of the sequences of instructions contained in the working memory 535 might cause the processor(s) 510 to perform one or more procedures of the methods described herein.

The terms "machine readable medium" and "computer readable medium," as used herein, refer to any medium that participates in providing data that causes a machine to operate in a specific fashion. In an embodiment implemented using the computer or hardware system 500, various computer readable media might be involved in providing instructions/code to processor(s) 510 for execution and/or might be used to store and/or carry such instructions/code (e.g., as signals). In many implementations, a computer readable medium is a non-transitory, physical, and/or tangible storage medium. In some embodiments, a computer readable medium may take many forms, including, but not limited to, non-volatile media, volatile media, or the like. Non-volatile media includes, for example, optical and/or magnetic disks, such as the storage device(s) 525. Volatile media includes, without limitation, dynamic memory, such as the working memory 535. In some alternative embodiments, a computer readable medium may take the form of transmission media, which includes, without limitation, coaxial cables, copper wire, and fiber optics, including the wires that comprise the bus 505, as well as the various components of the communication subsystem 530 (and/or the media by which the communications subsystem 530 provides communication with other devices). In an alternative set of embodiments, transmission media can also take the form of waves (including without limitation radio, acoustic, and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 510 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer or hardware system 500. These signals, which might be in the form of electromagnetic signals, acoustic signals, optical signals, and/or the like, are all examples of carrier waves on which instructions can be encoded, in accordance with various embodiments of the invention.

The communications subsystem 530 (and/or components thereof) generally will receive the signals, and the bus 505 then might carry the signals (and/or the data, instructions, etc. carried by the signals) to the working memory 535, from which the processor(s) 505 retrieves and executes the instructions. The instructions received by the working memory 535 may optionally be stored on a storage device 525 either before or after execution by the processor(s) 510.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A method, comprising:
    monitoring one or more ambient environmental conditions near or around a user or patient;
    receiving physiological data of the user or patient at a computer system, the physiological data comprising photoplethysmograph (PPG) waveform data;
    analyzing the PPG waveform data against a compensatory reserve index model of PPG waveform data representing a combination of a plurality of postures and motions of the user or patient;
    determining at least one physiological state of the user or patient, based at least in part on the analysis of the PPG waveform data of the user or patient, using the computer system, wherein the at least one physiological state of the user or patient comprises a hydration state of the user or patient;

sending the determined at least one physiological state of the user or patient from the computer system to a user or patient device; and outputting one or more display signals from the computer system to the user or patient device for displaying on a display screen of the user or patient devices the determined at least one physiological state of the user.

2. The method of claim 1, further comprising:

monitoring the physiological data of the user or patient using one or more sensors that sense the PPG waveform data and at least one of the plurality of postures or motions of the user or patient; and sending the monitored physiological data including the monitored plurality of postures or the plurality of motions from the one or more sensors to the computing system.

3. The method of claim 2, further comprising:

monitoring the at least one physiological state of the user or patient using the one or more sensors, wherein each of the one or more sensors one or more sensors measuring hemodynamic status of the user; one or more sensors measuring closeness of hemodynamic collapse due to at least one of heat stress, hydration, or central fluid loss; one or more sensors that continuously capture one or more pulsatile components of a cardiac cycle of the user or patient; one or more electrocardiograph sensors; or one or more respiration rate sensors; wherein the one or more sensors that continuously capture the one or more pulsatile components of the cardiac cycle of the user or patient comprises at least one of radio frequency ("RF") sensor, a PPG, a volume clamp, or a continuous blood pressure ("BP") sensor;

monitoring the one or more ambient environmental conditions using one or more additional sensors, wherein the one or more ambient environmental conditions each comprises one of moisture, humidity, rainfall, temperature, atmospheric pressure, air quality, windspeed, windchill, or altitude;

receiving the monitored physiological state of the user or patient at the computing system; and receiving the monitored one or more ambient environmental conditions at the computing system;

wherein determining the at least one physiological state of the user or patient using the computing system comprises determining at least one physiological state of the user or patient based at least in part on the identified one or more ambient environmental conditions.

4. The method of claim 1, wherein the at least one physiological state of the user or patient comprises at least one of a dehydration state of the user or patient, a fitness state of the user or patient, a health state of the user or patient, an exertion readiness state of the user or patient, a fatigue state of the user or patient, an alertness level of the user or patient, an altitude sickness state of the user or patient, a level of tolerance to heat of the user or patient, a level of tolerance to cold of the user or patient, a level of tolerance to other environmental conditions of the user or patient, a level of tolerance to liquid limitations of the user or patient, a level of tolerance to blood loss of the user or patient, or one or more states of illness of the user or patient.

5. The method of claim 1, further comprising:

storing a log including one or more recordings of previous commands issued by the user or patient in the user or patient device, respectively, the log including a recording of the commands;

wherein when the commands comprise verbal commands and the method further comprises determining an irregular speech pattern in the verbal command issued by the user or patient using the computing system;

wherein the at least one physiological state of the user or patient is further determined based at least in part on determination of a presence of the irregular speech pattern.

6. The method of claim 5, further comprising:

monitoring physiological data indicative of sodium content of the user's or patient's perspiration using one or more first sensors;

wherein the at least one physiological state of the user or patient comprises hyponatremia or hypernatremia, wherein the method further comprises determining whether the user or patient is in the state of hyponatremia or hypernatremia using the computer system based, at least in part, on the physiological data indicative of sodium content of the user's or patient's perspiration.

7. The method of claim 1 further comprising:

generating motion data indicative of user or patient movement using one or more of the sensors;

sending the motion data from the one or more sensors to the computing system; and mitigating motion artifacts from the PPG waveform data of the physiological data using the computing system, based, at least in part, on the motion data.

8. The method as in claim 1 wherein the physiological data further comprises electrocardiograph data.

9. An apparatus, comprising:

at least one processor; and a non-transitory computer readable medium communicatively coupled to the at least one processor, the non-transitory computer readable medium having stored thereon computer software comprising a set of instructions that, when executed by the at least one processor, causes the apparatus to:

monitor one or more ambient environmental conditions near or around a user or patient;

receive physiological data of the user or patient, the physiological data comprising photoplethysmograph (PPG) waveform data;

analyzing the PPG waveform data against a compensatory reserve index model of PPG waveform data representing a combination of a plurality of postures and motions of the user or patient;

determine at least one physiological state of the user or patient, based at least in part on the analysis of the PPG waveform data, wherein the at least one physiological state of the user or patient comprises a hydration state of the user or patient;

send the determined at least one physiological state of the user or patient to a user or patient device; and output one or more display signals to a user or patient device for displaying the determined at least one physiological state of the user.

10. The apparatus of claim 9, wherein the set of instructions are further executable by the at least one processor to:

monitor the physiological data of the user or patient and at least one of the plurality of postures or one the plurality of motions of the user or patient using one or more sensors; and send the monitored physiological data and the data regarding the monitored plurality of postures or the plurality of motions of the user or patient from the one or more sensors to the computing systems.

11. The apparatus as in claim 9 wherein the physiological data further comprises electrocardiograph data.

12. A system, comprising:
one or more sensors, wherein the one or more sensors are configured to monitor at least physiological data of a user or patient, the physiological data comprising photoplethysmograph (PPG) waveform data and send the physiological data to a computer system, and one or more additional sensors to monitor one or more ambient environmental conditions around or near the user or patient, wherein the computing system comprises:
at least one first processor; and
a first non-transitory computer readable medium communicatively coupled to the at least one first processor, the first non-transitory computer readable medium having stored thereon computer software comprising a first set of instructions that, when executed by the at least one first processor, causes the computing system to:
receive the physiological data of a user or patient;
analyze the PPG waveform data against a compensatory reserve index model of PPG waveform data representing a combination of a plurality of postures and motions of the user or patient;
determine at least one physiological state of the user or patient, based at least in part on the analysis of the PPG waveform data and at least one of one or more postures or one or more motions of the user or patient, wherein the at least one physiological state of the user or patient comprises a hydration state of the user or patient;
send the determined at least one physiological state of the user or patient to a user or patient device; and
display the determined at least one physiological state of the user or patient on a display screen of the user or patient device, respectively.

13. The system of claim 12, wherein the one or more sensors are each encapsulated within a sensor device, wherein each sensor device comprises one of a patch-based sensor device, a wrist strap-based sensor device, an arm strap-based sensor device, a head band-based sensor device, a belt-based sensor device, a leg strap-based sensor device, an ankle strap-based sensor device, or a shoe strap-based sensor device.

14. The system of claim 12, further comprising:
the user or patient device, comprising:
a user interface;
at least one second processor; and
a second non-transitory computer readable medium communicatively coupled to the at least one second processor, the second non-transitory computer readable medium having stored thereon computer software comprising a second set of instructions that, when executed by the at least one second processor, causes the user or patient device to:
receive at the user interface a command to initiate sensor recording; and
send the received command to initiate sensor recording to the one or more sensors, wherein, in response to receiving the command to initiate sensor recording, the one or more sensors initiate sensor recording to monitor at least one of the plurality of postures or one the plurality of motions of the user or patient;
wherein the first set of instructions further comprise instructions, when executed by the at least one first processor, further causes the computing system to store an association between the initiated sensor recording and the PPG waveform data and the one or more postures or one or more motions of the user or patient in a data store corresponding to the received command,
wherein the one or more sensors send data regarding the monitored at least one of the one or more postures or one or more motions of the user or patient to the computing system.

15. The system of claim 12 wherein the one or more sensors comprises one or more sensors to measure a hemodynamic status of the user or patient; one or more sensors to measure closeness of hemodynamic collapse due to at least one of heat stress, hydration, or central fluid loss; one or more sensors to continuously capture one or more pulsatile components of a cardiac cycle of the user or patient; one or more electrocardiograph sensors; or one or more respiration rate sensors; wherein the one or more sensors that continuously capture the one or more pulsatile components of the cardiac cycle of the user or patient comprises at least one of radio frequency ("RF") sensor, a PPG, a volume clamp, or a continuous blood pressure ("BP") sensor;
wherein the first set of executable instructions further comprise instructions when executed by the at least one first processor, further causes the computing system to receive the monitored physiological state of the user or patient.

16. The system of claim 12, wherein the first set of instructions are further executable by the at least one processor to:
receive a log including one or more recordings of previous commands issued by the user or patient from a user or patient device, the commands comprising verbal commands and the log comprising a recording of the verbal command;
determine a presence of an irregular speech pattern in the verbal commands issued by the user;
wherein the at least one physiological state of the user or patient is determined based at least in part on determination of the presence of the irregular speech pattern.

17. The system of claim 12, wherein the first set of instructions are further executable by the at least one processor to:
monitor physiological data indicative of sodium content of the user's or patient's perspiration using the one or more first sensors; and
wherein the at least one physiological state of the user or patient comprises hyponatremia or hypernatremia, wherein the first set of executable instructions yet further comprises instructions to determine whether the user or patient is in the physiological state of hyponatremia or hypernatremia based, at least in part, on the physiological data indicative of sodium content of the user's or patient's perspiration.

18. The system as in claim 12 wherein the physiological data further comprises electrocardiograph data.

* * * * *